(12) United States Patent
Xu et al.

(10) Patent No.: US 6,413,758 B1
(45) Date of Patent: Jul. 2, 2002

(54) **METHOD FOR CLONING AND EXPRESSION OF BPML RESTRICTION ENDONUCLEASE IN *E. COLI***

(75) Inventors: Shuang-yong Xu, Lexington; Jian-ping Xiao, Wenham; Zhenyu Zhu, Beverly, all of MA (US)

(73) Assignee: New England Biolabs, Inc., Beverly, MA (US)

(*) Notice: Subject to any disclaimer, the term of this patent is extended or adjusted under 35 U.S.C. 154(b) by 0 days.

(21) Appl. No.: 09/693,146

(22) Filed: Oct. 20, 2000

(51) Int. Cl.[7] .............................. C12N 9/22; C12N 15/55
(52) U.S. Cl. ................. 435/199; 435/252.3; 435/320.1; 536/23.2
(58) Field of Search .................... 435/320.1, 252.3, 435/199; 536/23.2

(56) References Cited

U.S. PATENT DOCUMENTS

| | | | |
|---|---|---|---|
| 5,200,333 A | 4/1993 | Wilson | 435/122.3 |
| 5,498,535 A | 3/1996 | Fomenkov et al. | 435/122.3 |

OTHER PUBLICATIONS

MBI Fermentas 2000–2001 Catalog, p. No. 56, Gsul, Product No. ER0461/ER0462.
Roberts and Macelis, Nucleic Acids Res. 27:312–313 (1999).
Kosykh, et al., Mol. Gen. Genet. 178:717–719 (1980).
Mann, et al., Gene, 3:97–112 (1978).
Walder, et al., Proc. Natl. Acad. Sci. 78:1503–1507 (1981).
Bougueleret, et al., Nucleic Acids Res. 12:3659–3676 (1984).
Gingeras and Brooks, Proc. Natl. Acad. Sci. USA 80:402–406 (1983).
Theriault and Roy, Gene 19:355–359 (1982).
Blumenthal, et al., J. Bacteriology 164:501–509 (1985).
Wayne, et la., Gene 202:83–88 (1997).
Kiss, et al., Nucleic Acids Res. 13:6403–6421 (1985).
Szomolanyi, et al., Gene 10:219–225 (1980).
Janulaitis, et al., Gene 20:197–204 (1982).
Kiss and Baldauf, Gene 21:111–119 (1983).
Walder, et al., J. Biol. Chem. 258:1235–1241 (1983).
Fomenkov, et al., Nucleic Acids Res. 22:2399–2403 (1994).
Janulaitis, et al., Nucleic Acids Res. 20:6051–6056 (1992).
Piekarowicz, et al., J. Mol. Biol. 293:1055–1065 (1999).
Sethmann, et al., EMBO Journal 18:3502–3508 (1999).

*Primary Examiner*—Charles L. Patterson, Jr.
(74) *Attorney, Agent, or Firm*—Gregory D. Williams

(57) ABSTRACT

The present invention relates to recombinant DNA which encodes the BpmI restriction endonuclease as well as BpmI methyltransferase, expression of BpmI restriction endonuclease from *E. coli* cells containing the recombinant DNA. BpmI endonuclease is a fusion of two distinct elements with a possible structural domains of restriction-methylation-specificity (R-M-S). This domain organization is analogous to the type I restriction-modification system with three distinct subunits, restriction, methylation, and specificity (R, M, and S). Because BpmI is quite distinct to other type IIs restriction enzymes, it is proposed that BpmI belongs to a subgroup of type II restriction enzymes called type IIf (f stands for fusion of restriction-modification-specificity domains). The Type IIf group of restriction enzyme includes Eco57I, BpmI, GsuI, BseRI and some other restriction enzymes that cut downstream sequences at long distance, 10–20 bp downstream of recognition sequence, such as MmeI (N20/N18)).

6 Claims, 7 Drawing Sheets

FIG. 2A

```
     ATGAATCAATTAATTGAAAATGTTAATCTACAAAAATTAAGGGGTGGGTATTACACCCCT
  1  ------------+---------+---------+---------+---------+---------+  60
      M  N  Q  L  I  E  N  V  N  L  Q  K  L  R  G  G  Y  Y  T  P
     AAAGTTATTGCTGACTTTTTATGTCAATGGAGTATTCAAGATGACACAAAGAGTGTACTT
 61  ------------+---------+---------+---------+---------+---------+ 120
      K  V  I  A  D  F  L  C  Q  W  S  I  Q  D  D  T  K  S  V  L
     GAACCCAGTTGTGGAGATGGTAATTTTATTGAATCGGCAATACTTAGGTTCAAAGAACTT
121  ------------+---------+---------+---------+---------+---------+ 180
      E  P  S  C  G  D  G  N  F  I  E  S  A  I  L  R  F  K  E  L
     AGTATAGATAATGAACAACTTAAAGGAAGAATTACAGGAGTAGAGCTAATTGAAGAAGAA
181  ------------+---------+---------+---------+---------+---------+ 240
      S  I  D  N  E  Q  L  K  G  R  I  T  G  V  E  L  I  E  E  E
     GCTTTGAAAGTTCAAAATCGAGCAAATGAGTTGGGGGTTGATAAAAACTCAATAGTAAAT
241  ------------+---------+---------+---------+---------+---------+ 300
      A  L  K  V  Q  N  R  A  N  E  L  G  V  D  K  N  S  I  V  N
     AGTGACTTCTTTCAATTTGTAAAAGATAATAAGAATAAAAAATTTGATACTATTATTGGT
301  ------------+---------+---------+---------+---------+---------+ 360
      S  D  F  F  Q  F  V  K  D  N  K  N  K  K  F  D  T  I  I  G
     AATCCACCATTCATAAGATACCAAAACTTTCCTGAAGAGCATCGTAGTATAGCCATGGAA
361  ------------+---------+---------+---------+---------+---------+ 420
      N  P  P  F  I  R  Y  Q  N  F  P  E  E  H  R  S  I  A  M  E
     ATGATGGAGGAACTAGGTTTAAAACCTAATAAACTTACAAATATCTGGGTTCCATTTCTA
421  ------------+---------+---------+---------+---------+---------+ 480
      M  M  E  E  L  G  L  K  P  N  K  L  T  N  I  W  V  P  F  L
     GTGGTATCTGCTACATTACTTAATGAACAAGGAAAGATGGCTATGGTTATACCGGCTGAA
481  ------------+---------+---------+---------+---------+---------+ 540
      V  V  S  A  T  L  L  N  E  Q  G  K  M  A  M  V  I  P  A  E
     TTATTTCAGGTAAAGTATGCAGCAGAAACAAGAATTTTTTTATCAAAGTTTTTCGATCGT
541  ------------+---------+---------+---------+---------+---------+ 600
      L  F  Q  V  K  Y  A  A  E  T  R  I  F  L  S  K  F  F  D  R
     ATCACTATAATTACATTTGAAAAACTTGTTTTTGAAAATATCCAACAGGAAGTTATACTA
601  ------------+---------+---------+---------+---------+---------+ 660
      I  T  I  I  T  F  E  K  L  V  F  E  N  I  Q  Q  E  V  I  L
     CTTCTTTGTGAAAAGAAAGTTAATAAAGGTAAAGGAATTCGGGTTATTGAATGCGAGAAC
661  ------------+---------+---------+---------+---------+---------+ 720
      L  L  C  E  K  K  V  N  K  G  K  G  I  R  V  I  E  C  E  N
     TTAGATGGATTAAATTCCATTGATTTTGTAGCTATAAATGGTTCAAATGTTAAACCTATT
721  ------------+---------+---------+---------+---------+---------+ 780
      L  D  G  L  N  S  I  D  F  V  A  I  N  G  S  N  V  K  P  I
     GAACACCGTACTGAAAAGTGGACAAAGTATTTCTTAAACGAAGATGAAATACTTCTTTTA
781  ------------+---------+---------+---------+---------+---------+ 840
      E  H  R  T  E  K  W  T  K  Y  F  L  N  E  D  E  I  L  L  L
     CAGAGTTTAAAGGAAGACAAACGCGTTAAAAATTGTAATGACTATTTTAAGACAGAAGTT
841  ------------+---------+---------+---------+---------+---------+ 900
      Q  S  L  K  E  D  K  R  V  K  N  C  N  D  Y  F  K  T  E  V
     GGCTTAGTTACTGGACGAAACGAATTCTTTATGATGAAAGAAAACCAAGTAAAAGAATGG
901  ------------+---------+---------+---------+---------+---------+ 960
      G  L  V  T  G  R  N  E  F  F  M  M  K  E  N  Q  V  K  E  W
     AATCTAGAAGAATATACAATACCTGTTACAGGTAGGTCCAATCAGTTAAAAGGTATAACA
961  ------------+---------+---------+---------+---------+---------+ 1020
      N  L  E  E  Y  T  I  P  V  T  G  R  S  N  Q  L  K  G  I  T
```

FIG. 2B

```
     TTTACAGAAAATGATTTTCATGAAAATTCAATGGAACAAAAGGCAATTCACCTATTTTTG
1021 ------------+---------+---------+---------+---------+---------+ 1080
      F  T  E  N  D  F  H  E  N  S  M  E  Q  K  A  I  H  L  F  L
     CCACCAGATGAAGATTTTGAAAAGTTACCGATTGAGTGTCAAAATTATATCAAGTATGGG
1081 ------------+---------+---------+---------+---------+---------+ 1140
      P  P  D  E  D  F  E  K  L  P  I  E  C  Q  N  Y  I  K  Y  G
     GAAGAAAAAGGCTTCCATCAAGGCTATAAAACCAGAATTAGAAAACGTTGGTATATAACT
1141 ------------+---------+---------+---------+---------+---------+ 1200
      E  E  K  G  F  H  Q  G  Y  K  T  R  I  R  K  R  W  Y  I  T
     CCATCTAGATGGGTTCCAGATGCTTTTGCTTTAAGACAGGTTGATGGCTATCCAAAACTA
1201 ------------+---------+---------+---------+---------+---------+ 1260
      P  S  R  W  V  P  D  A  F  A  L  R  Q  V  D  G  Y  P  K  L
     ATTTTAAATGAAACCGACGCTTCTTCTACTGATACAATTCATAGGGTTAGATTTAAAGAA
1261 ------------+---------+---------+---------+---------+---------+ 1320
      I  L  N  E  T  D  A  S  S  T  D  T  I  H  R  V  R  F  K  E
     GGTATAAATGAAAAGTTAGCCGTAGTTTCATTTTTGAACTCACTCACTTTTGCATCTTCA
1321 ------------+---------+---------+---------+---------+---------+ 1380
      G  I  N  E  K  L  A  V  V  S  F  L  N  S  L  T  F  A  S  S
     GAAATAACGGGGAGAAGTTATGGTGGTGGTGTTATGACATTCGAACCAACTGAAATTGGA
1381 ------------+---------+---------+---------+---------+---------+ 1440
      E  I  T  G  R  S  Y  G  G  G  V  M  T  F  E  P  T  E  I  G
     GAAATCCTAATACCTTCCTTTGATAACTTATCCATTGATTTTGATAAAATTGATGCCTTA
1441 ------------+---------+---------+---------+---------+---------+ 1500
      E  I  L  I  P  S  F  D  N  L  S  I  D  F  D  K  I  D  A  L
     ATTCGAGAAAAGGAGATTGAAAAAGTCCTTGATATTGTTGATGAAGCTTTACTTATAAAA
1501 ------------+---------+---------+---------+---------+---------+ 1560
      I  R  E  K  E  I  E  K  V  L  D  I  V  D  E  A  L  L  I  K
     TATCATGGGTTTAGTGAGAAAGAAGTAAAACAGCTTCGAGGGATATGGAAGAAACTTTCT
1561 ------------+---------+---------+---------+---------+---------+ 1620
      Y  H  G  F  S  E  K  E  V  K  Q  L  R  G  I  W  K  K  L  S
     CAGAGAAGAAACAATAGAACGAAGAAATAA
1621 ------------+---------+--------+ 1650
      Q  R  R  N  N  R  T  K  K  *
```

FIG. 3A

```
    ATGCATATAAGTGAGTTAGTAGATAAATACAAAGCGCATAGAAGTACTTTTTTAAAACCA
1   ------------+---------+---------+---------+---------+---------+   60
     M  H  I  S  E  L  V  D  K  Y  K  A  H  R  S  T  F  L  K  P
    ACTTATAATGAAACTCAACTAAGGAATGATTTTATAGACCCACTTCTAAAATCTTTAGGA
61  ------------+---------+---------+---------+---------+---------+   120
     T  Y  N  E  T  Q  L  R  N  D  F  I  D  P  L  L  K  S  L  G
    TGGGATGTTGATAATACCAAAGGAAAAACACATATTCTAAGAGATGTCATTCAAGAAGAA
121 ------------+---------+---------+---------+---------+---------+   180
     W  D  V  D  N  T  K  G  K  T  H  I  L  R  D  V  I  Q  E  E
    TACATAGAAATAAAAGATGAGGAGACAAAGAAAAATCCAGATTATACACTTCGTATAAAC
181 ------------+---------+---------+---------+---------+---------+   240
     Y  I  E  I  K  D  E  E  T  K  K  N  P  D  Y  T  L  R  I  N
    GGTACGAGAAAGCTGTTTGTAGAGGTTAAGAAACCGTCTTTTAATATTTTGAAATCAGCT
241 ------------+---------+---------+---------+---------+---------+   300
     G  T  R  K  L  F  V  E  V  K  K  P  S  F  N  I  L  K  S  A
    AAAGCAGCCTTCCAAACAAGAAGATATGGTTGGAGTGCTAACCTTGGTATTTCAGTACTT
301 ------------+---------+---------+---------+---------+---------+   360
     K  A  A  F  Q  T  R  R  Y  G  W  S  A  N  L  G  I  S  V  L
    ACAAATTTCGAGCATCTAGTTATTTATGATTGTAGATATACGCCTGACAAATCCGACAAT
361 ------------+---------+---------+---------+---------+---------+   420
     T  N  F  E  H  L  V  I  Y  D  C  R  Y  T  P  D  K  S  D  N
    GAACATATTGCTAGATATAAAGTTTTCTCTTACGAGGAATATGAAGAAGCATTTGATGAA
421 ------------+---------+---------+---------+---------+---------+   480
     E  H  I  A  R  Y  K  V  F  S  Y  E  E  Y  E  E  A  F  D  E
    ATAAAGGATATAATTTCATATGAGTCAGCCAACTCAGGTGCTCTGGACGAAATGTTTGAT
481 ------------+---------+---------+---------+---------+---------+   540
     I  K  D  I  I  S  Y  E  S  A  N  S  G  A  L  D  E  M  F  D
    GTAAATACAAGAGTTGGTGAAACGTTTGACGAGTATTTTTTACAGCAAATTGAGAATTGG
541 ------------+---------+---------+---------+---------+---------+   600
     V  N  T  R  V  G  E  T  F  D  E  Y  F  L  Q  Q  I  E  N  W
    CGCGAAAAGCTAGCTAAAACTGCAATTAAAAATAACACCGAATTAGGTGAAGAGGACGTC
601 ------------+---------+---------+---------+---------+---------+   660
     R  E  K  L  A  K  T  A  I  K  N  N  T  E  L  G  E  E  D  V
    AATTTTATTGTCCAAAGACTATTAAACAGAATTATTTTTCTTAGAGTTTGTGAAGATAGA
661 ------------+---------+---------+---------+---------+---------+   720
     N  F  I  V  Q  R  L  L  N  R  I  I  F  L  R  V  C  E  D  R
    ACCATTGAAAAATATGAAACAATTAAAAGTATAAAAAACTATGAGGAATTAAAAGATCTG
721 ------------+---------+---------+---------+---------+---------+   780
     T  I  E  K  Y  E  T  I  K  S  I  K  N  Y  E  E  L  K  D  L
    TTTCAAAAGTCTGATAGGAAATTTAATTCAGGTCTCTTTGACTTCATAGATGATACGCTC
781 ------------+---------+---------+---------+---------+---------+   840
     F  Q  K  S  D  R  K  F  N  S  G  L  F  D  F  I  D  D  T  L
    TTGCTTGAGGTTGAAATTGATTCGAATGTATTGATAGAAATTTTTAGTGATTTATATTTC
841 ------------+---------+---------+---------+---------+---------+   900
     L  L  E  V  E  I  D  S  N  V  L  I  E  I  F  S  D  L  Y  F
    CCACAAAGCCCATATGATTTTTCTGTTGTCGATCCAACAATATTAAGCCAGATATATGAA
901 ------------+---------+---------+---------+---------+---------+   960
     P  Q  S  P  Y  D  F  S  V  V  D  P  T  I  L  S  Q  I  Y  E
    CGTTTTCTAGGTCAAGAAATAATTATAGAGTCAGGTGGTACATTTCACATTACGGAGTCA
961 ------------+---------+---------+---------+---------+---------+   1020
     R  F  L  G  Q  E  I  I  I  E  S  G  G  T  F  H  I  T  E  S
```

FIG. 3B

```
     CCAGAAGTTGCGGCGTCCAATGGTGTTGTTCCAACTCCAAAAATTATCGTCGAACAGATA
1021 ------------+----------+----------+----------+----------+----------+ 1080
      P  E  V  A  A  S  N  G  V  V  P  T  P  K  I  I  V  E  Q  I
     GTGAAAGACACTTTAACGCCCCTTACGGAAGGCAAAAAATTTAATGAGCTATGTAACTTA
1081 ------------+----------+----------+----------+----------+----------+ 1140
      V  K  D  T  L  T  P  L  T  E  G  K  K  F  N  E  L  C  N  L
     AAAATAGCAGATATATGTTGTGGATCAGGAACTTTCCTAATTTCAAGTTATGACTTTCTA
1141 ------------+----------+----------+----------+----------+----------+ 1200
      K  I  A  D  I  C  C  G  S  G  T  F  L  I  S  S  Y  D  F  L
     GTAGAGAAAGTAATGGAAAAGATAATAGAAGAGAACATCGATGATTCAGATTTAGTATAT
1201 ------------+----------+----------+----------+----------+----------+ 1260
      V  E  K  V  M  E  K  I  I  E  E  N  I  D  D  S  D  L  V  Y
     GAAACTGAAGAAGGGCTAATTTTGACACTTAAAGCAAAAAGAAATATCTTGGAGAATAAT
1261 ------------+----------+----------+----------+----------+----------+ 1320
      E  T  E  E  G  L  I  L  T  L  K  A  K  R  N  I  L  E  N  N
     TTGTTTGGTGTTGATGTTAATCCATACGCTGTTGAAGTAGCTGAGTTCAGTTTATTATTA
1321 ------------+----------+----------+----------+----------+----------+ 1380
      L  F  G  V  D  V  N  P  Y  A  V  E  V  A  E  F  S  L  L  L
     AAGCTATTAGAAGGTGAGAATGAGGCATCGGTTAATAATTTCATTCACGAGCATGAGGAT
1381 ------------+----------+----------+----------+----------+----------+ 1440
      K  L  L  E  G  E  N  E  A  S  V  N  N  F  I  H  E  H  E  D
     AAAATATTACCGGATTTAACATCTATTATTAAATGTGGAAACAGCTTAGTAGATAATAAG
1441 ------------+----------+----------+----------+----------+----------+ 1500
      K  I  L  P  D  L  T  S  I  I  K  C  G  N  S  L  V  D  N  K
     TTTTTTGAATTCATGCCAGAATCGTTAGAGGACGATGAAATCTTATTTAAGGCTAATCCA
1501 ------------+----------+----------+----------+----------+----------+ 1560
      F  F  E  F  M  P  E  S  L  E  D  D  E  I  L  F  K  A  N  P
     TTTGAATGGGAAGAGGAGTTTCCAGATATTATGGCAAATGGTGGCTTTGATGCTATTATA
1561 ------------+----------+----------+----------+----------+----------+ 1620
      F  E  W  E  E  E  F  P  D  I  M  A  N  G  G  F  D  A  I  I
     GGAAATCCACCTTATGTTCGAATACAGAACATGAAAAAATATAGTCCTGAGGAAATTGAA
1621 ------------+----------+----------+----------+----------+----------+ 1680
      G  N  P  P  Y  V  R  I  Q  N  M  K  K  Y  S  P  E  E  I  E
     TATTATCAATCAAAAGACTCTGAATATACTGTTGCAAAAAAAGAAACAGTTGACAAGTAT
1681 ------------+----------+----------+----------+----------+----------+ 1740
      Y  Y  Q  S  K  D  S  E  Y  T  V  A  K  K  E  T  V  D  K  Y
     TTTTTATTTATTGAGAGAGCATTAATATTACTCAATCCTACTGGGCTGTTGGGTTATATA
1741 ------------+----------+----------+----------+----------+----------+ 1800
      F  L  F  I  E  R  A  L  I  L  L  N  P  T  G  L  L  G  Y  I
     ATACCGCATAAAATTCTTTATTACAAAAGGTGGTAAGGAACTAAGAAAGTTCATAGCTGAA
1801 ------------+----------+----------+----------+----------+----------+ 1860
      I  P  H  K  F  F  I  T  K  G  G  K  E  L  R  K  F  I  A  E
     AAACATCAAATATCAAAAATTATAAATTTTGGTGTTACACAGGTCTTTCCAGGAAGAGCG
1861 ------------+----------+----------+----------+----------+----------+ 1920
      K  H  Q  I  S  K  I  I  N  F  G  V  T  Q  V  F  P  G  R  A
     ACATATACGGCTATTTTAATTATCCAAGCAAATAAAATGGCACAGTTCAAGTATAAGAAA
1921 ------------+----------+----------+----------+----------+----------+ 1980
      T  Y  T  A  I  L  I  I  Q  A  N  K  M  A  Q  F  K  Y  K  K
     GTAAGTAATATATCAGCAGAAACCCTAGATTCTGAAGAAAATACGTGTGTTTATAGCTCA
1981 ------------+----------+----------+----------+----------+----------+ 2040
      V  S  N  I  S  A  E  T  L  D  S  E  E  N  T  C  V  Y  S  S
```

FIG. 3C

```
     GAAAAGTATAATTCTGACCCTTGGATATTTTTATCTCCTGAAACAGAAGCTGTTTTTACT
2041 ---------+---------+---------+---------+---------+---------+ 2100
      E K Y N S D P W I F L S P E T E A V F T
     AAATTTACAGAAGCTCAATTTGAGAAACTTGGAGAAATCACTGATATAAGTGTAGGACTA
2101 ---------+---------+---------+---------+---------+---------+ 2160
      K F T E A Q F E K L G E I T D I S V G L
     CAAACAAGCGCTGATAAAATATATATTTTTATTCCTGAAAATGAAACTTCAGATACATAT
2161 ---------+---------+---------+---------+---------+---------+ 2220
      Q T S A D K I Y I F I P E N E T S D T Y
     ATATTTAATTATAAAGGGAAAAGATATGAAATAGAAAAATCTATATGTTGCCCAGCTATC
2221 ---------+---------+---------+---------+---------+---------+ 2280
      I F N Y K G K R Y E I E K S I C C P A I
     TATGACTTATCTTTTGGTTCTTTTGAAAGCATTCAGGGAAATGCACAAATGATATTCCCT
2281 ---------+---------+---------+---------+---------+---------+ 2340
      Y D L S F G S F E S I Q G N A Q M I F P
     TATGAAATCAGAGATGAAGAAGCATATCTACTAGAGGAAGAAACGCTTGAAAATGATTAT
2341 ---------+---------+---------+---------+---------+---------+ 2400
      Y E I R D E E A Y L L E E E T L E N D Y
     CCTCTTGCTTGGAATTATTTGAATGAGTTTAAAGAAGCTCTTGAAAAAAGAAGCTTACAA
2401 ---------+---------+---------+---------+---------+---------+ 2460
      P L A W N Y L N E F K E A L E K R S L Q
     GGCCGTAATCCGAAATGGTATCAATATGGTCGGTCCCAAAGTTTATCAAAATTTCATGAT
2461 ---------+---------+---------+---------+---------+---------+ 2520
      G R N P K W Y Q Y G R S Q S L S K F H D
     AAAGAAAAACTGATATGGACCGTACTTGCTACGAAACCCCCGTATGTACTTGATAGGAAT
2521 ---------+---------+---------+---------+---------+---------+ 2580
      K E K L I W T V L A T K P P Y V L D R N
     AACCTGTTATTTACTGGTGGTGGAAACGGACCGTATTATGGTTTAATTAACCAATCTATT
2581 ---------+---------+---------+---------+---------+---------+ 2640
      N L L F T G G G N G P Y Y G L I N Q S I
     TACTCTTTGCATTATTTTTTAGGTATTCTTTCACATCCTGTAATAGAAAGTATGGTAAAA
2641 ---------+---------+---------+---------+---------+---------+ 2700
      Y S L H Y F L G I L S H P V I E S M V K
     GCAAGGGCCAGTGAATTTAGGGGATCATATTATTCTCATGGAAAACAATTTATTGAGAAA
2701 ---------+---------+---------+---------+---------+---------+ 2760
      A R A S E F R G S Y Y S H G K Q F I E K
     ATCCCAATTAGAAAGATTGATTTTGATGATCAAGATGAGGTAGACAAATATAATACGGTG
2761 ---------+---------+---------+---------+---------+---------+ 2820
      I P I R K I D F D D Q D E V D K Y N T V
     GTCACAACAGTAGAAAAATTAATTATAACTACCGATAGAATTAAAAGTGAGAGCAATGGA
2821 ---------+---------+---------+---------+---------+---------+ 2880
      V T T V E K L I I T T D R I K S E S N G
     CCCCGGAGGAGAATGTTAAGAAGAAGGTTAGATGCTTTGTCTAATCAACTTATCCAGGTT
2881 ---------+---------+---------+---------+---------+---------+ 2940
      P R R R M L R R R L D A L S N Q L I Q V
     ATTAATGAACTTTATAATATCAGTGACGAAGAATATACGACAGTTTTGAATGATGAAATG
2941 ---------+---------+---------+---------+---------+---------+ 3000
      I N E L Y N I S D E E Y T T V L N D E M
     TTGACAGCGGCGTTAGGAGAAGAAAAATGA
3001 ---------+---------+--------+ 3030
      L T A A L G E E K *
```

METHOD FOR CLONING AND EXPRESSION OF BPML RESTRICTION ENDONUCLEASE IN E. COLI

BACKGROUND OF THE INVENTION

The present invention relates to recombinant DNA which encodes the BpmI restriction endonuclease as well as BpmI methyltransferase and expression of BpmI restriction endonuclease from *E. coli* cells containing the recombinant DNA. BpmI is an isoschizomer of GsuI (Fermentas 2000–2001 Catalog, Product No. ER0461/ER0462).

Type II restriction endonucleases are a class of enzymes that occur naturally in bacteria and in some viruses. When they are purified away from other bacterial proteins, restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, *Nucl. Acids Res.* 27:312–313 (1999)).

Restriction endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3' respectively. *Escherichia coli* RY13, on the other hand, produces only one enzyme, EcoRI, which recognizes the sequence 5'G/AATTC3'.

A second component of bacterial restriction-modification (R-M) systems are the methyltransferases (methylases). These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group (C5-methyl cytosine, N4-methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. It is only unmodified, and therefore identifiably foreign DNA, that is sensitive to restriction endonuclease recognition and cleavage.

By means of recombinant DNA technology, it is now possible to clone genes and overproduce the enzymes in large quantities. The key to isolating clones of restriction endonuclease genes is to develop a simple and reliable method to identify such clones within complex genomic DNA libraries, i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

A large number of type II restriction-modification systems have been cloned. The first cloning method used bacteriophage infection as a means of identifying or selecting restriction endonuclease clones (EcoRII: Kosykh et al., *Mol. Gen. Genet.* 178:717–719 (1980); HhaII: Mann et al., *Gene* 3:97–112 (1978); PstI: Walder et al., *Proc. Nat. Acad. Sci.* 78:1503–1507 (1981)). Since the presence of restriction-modification systems in bacteria enable them to resist infection by bacteriophage, cells that carry cloned restriction-modification genes can, in principle, be selectively isolated as survivors from genomic DNA libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids. Res.* 12:3659–3676 (1984); PaeR7: Gingeras and Brooks, *Proc. Natl. Acad. Sci. USA* 80:402–406 (1983); Theriault and Roy, *Gene* 19:355–359 (1982); PvuII: Blumenthal et al., *J. Bacteriol.* 164:501–509 (1985); Tsp45I: Wayne et al. *Gene* 202:83–88 (1997)).

A third approach is to select for active expression of methylase genes (methylase selection) (U.S. Pat. No. 5,200,333 and BsuRI: Kiss et al., *Nucl. Acids. Res.* 13:6403–6421 (1985)). Since R-M genes are often closely linked together, both genes can often be cloned simultaneously. This selection does not always yield a complete restriction system however, but instead yields only the methylase gene (BspRI: Szomolanyi et al., *Gene* 10:219–225 (1980); BcnI: Janulaitis et al., *Gene* 20:197–204 (1982); BsuRI: Kiss and Baldauf, *Gene* 21:111–119 (1983); and MspI: Walder et al., *J. Biol. Chem.* 258:1235–1241 (1983)).

A more recent method, the "endo-blue method", has been described for direct cloning of restriction endonuclease genes in *E. coli* based on the indicator strain of *E. coli* containing the dinD: :lacZ fusion (Fomenkov et al., U.S. Pat. No. 5,498,535, (1996); Fomenkov et al., *Nucl. Acids Res.* 22:2399–2403 (1994)). This method utilizes the *E. coli* SOS response signals following DNA damages caused by restriction endonucleases or non-specific nucleases. A number of thermostable nuclease genes (TaqI, Tth111I, BsoBI, Tf nuclease) have been cloned by this method (U.S. Pat. No. 5,498,535).

Because purified restriction endonucleases, and to a lesser extent, modification methylases, are useful tools for creating recombinant molecules in the laboratory, there is a commercial incentive to obtain bacterial strains through recombinant DNA techniques that produce large quantities of restriction enzymes. Such overexpression strains should also simplify the task of enzyme purification.

SUMMARY OF THE INVENTION

The present invention relates to a method for cloning the BpmI restriction endonuclease from *Bacillus pumilus* into *E.coli* by methylase selection and inverse PCR amplification of the adjacent DNA of the BpmI methylase gene.

The present invention relates to recombinant BpmI and methods for producing the same. BpmI restriction endonuclease is found in the strain of *Bacillus pumilus* (New England Biolabs' strain collection #711). It recognizes double-stranded DNA sequence 5' CTGGAG 3' (or 5'CTCCAG3') and cleaves 16/14 bases downstream of its recognition sequence (N16/N14) to generate a 2-base 3' overhanging ends.

By methylase selection, a methylase gene with high homology to amino-methyltransferases (N6-adenine methylases) was found in a DNA library. This gene was named BpmI M1 gene (BpmIM1, 1650 bp), encoding a 549-aa protein with predicted molecular mass of 63,702 daltons. There was one partial open reading frame upstream of BpmIM1 gene that displayed 31% amino acid sequence identity to another restriction enzyme Eco57I with similar recognition sequence (Eco57I recognition sequence: 5'CTGAAG N16/N14; BpmI recognition sequence: 5' CTGGAG N16/N14; A. Janulaitis et al. *Nucl. Acids Res.* 20:6051–6056, (1992)).

In order to clone the rest of the BpmIRM gene, inverse PCR was used to amplify the adjacent DNA sequence. After four rounds of inverse PCR reactions, an open reading frame of 3030 bp was found upstream of BpmI M1 methylase gene, which encodes a 1009-aa protein with predicted molecular mass of 116,891 daltons. By amino acid sequence comparison of BpmI endonuclease with all known proteins in GenBank protein database, it was discovered that BpmI endonuclease is a fusion of two distinct elements with a possible structural domains of restriction-methylation-specificity (R-M-S). This domain organization is analogous to the type I restriction-modification system with three distinct subunits R, M, and S. Because BpmI is quite distinct to other type IIs restriction enzymes, it is proposed that BpmI belongs to a subgroup of type II restriction enzymes called type IIf (f stands for fusion of restriction-modification domains).

To generate a premodified expression host, the BpmIM1 gene was amplified in PCR and cloned in *E. coli* strain ER2566. BpmI M1 methylase also modifies XhoI site. XhoI recognition sequence 5' CTCGAG 3' is similar to BpmI recognition sequence 5' CTGGAG 3' with only one base difference. It was concluded that BpmI M1 methylase may recognize the sequence 5' CTNNAG 3' and possibly modify the adenine base to create N6-adenine in the symmetric sequence.

The expression of 3030-bp BpmIRM gene was quite difficult because of the large size of the PCR porduct. The BpmIRM gene was first amplified by Taq DNA polymerase and cloned into the premodified host, but no BpmI activity was detected. To improve the fidelity of PCR reaction, Deep Vent DNA polymerase was used in PCR. Among 18 clones with the insert, only one clone (#4) displayed partial BpmI activity. This clone was sequenced and confirmed to contain wild type sequence.

BRIEF DESCRIPTION OF THE DRAWINGS

FIG. 2 DNA sequence of BpmI M1 methylase gene (BpmIM1) (SEQ ID NO:1) and its encoded amino acid sequence (SEQ ID NO:2).

FIG. 3 DNA sequence of BpmI endonuclease gene (BpmIRM) (SEQ ID NO:3) and its encoded amino acid sequence (SEQ ID NO:4).

DETAILED DESCRIPTION OF THE INVENTION

Figure 1:
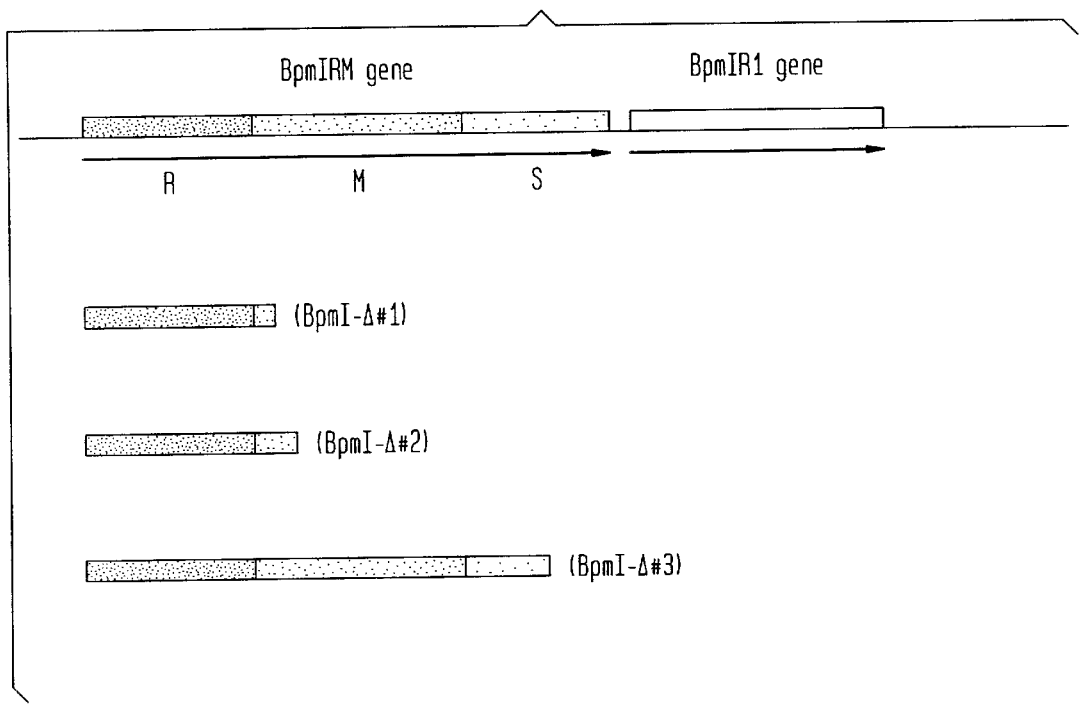
FIG. 1 Gene organization of BpmI restriction-modification system. Genes BpmIRM and BpmIM1 code for BpmI endonuclease (BpmI endonuclease-methylase fusion protein and BpmI M1, respectively. BpmI-Δ#1, BpmI-Δ#2, and BpmI-Δ#3 are deletion mutants with deletions in the methylation or specificity domains.

The method described herein by which the BpmI methylase gene and the BpmI restriction endonuclease genes are preferably cloned and expressed in *E. coli* employ the following steps:

1. Preparation of genomic DNA and restriction digestion of genomic DNA.

Genomic DNA is prepared from *Bacillus pumilus* (New England Biolabs collection #711) by the standard procedure. Five μg genomic DNA is digested partially with 2, 1, 0.5, and 0.25 units of ApoI (recognition sequence R/AATTY). Genomic DNA fragments in the range of 2–10 kb are purified through a low-melting agarose gel. Genomic and pBR322 DNA are also digested with AatII, BamHI, ClaI, EagI, EcoRI, HindIII, NdeI, NheI, SaI, and SphI, respectively, however, no methylase positive clones were obtained.

2. Construction of ApoI partial genomic DNA library and challenge of library with BpmI.

The ApoI partial DNA fragments are ligated to EcoRI digested and CIP treated pBR322 vector. The ligated DNA is transferred into *E. coli* RR1 competent cells by electroporation. Transformants are pooled and amplified. Plasmid DNA is prepared from the cells and challenged with BpmI. Following BpmI digestion, the challenged DNA is transformed into RR1 cells. Survivors are screened for resistance to BpmI digestion. Two resistant clones, #18 and #26, were identified to be resistant to BpmI digestion. AatII, BamHI, ClaI, EagI, EcoRI, HindIII, NdeI, NheI, SalI, and SphI digested genomic DNA were also ligated to pBR322 with compatible ends and genomic DNA libraries are constructed. However, no apparent BpmI resistant clones were discovered from these libraries.

3. Subcloning and DNA sequencing of the resistant clone.

One resistant clone #26 contained an insert of about 3.1 kb. The forward and reverse primers of pUC19 were used to sequence the insert. Three ApoI and one HindIII fragments were subcloned in pUC19 and sequenced. The entire insert was sequenced by primer walking. A methylase gene with high homology to amino-methyltransferase is found within the insert which is name BpmI M1 gene. The BpmIM1 gene is 1,650 bp, encoding a 549-amino acid protein with predicted molecular mass of 63,702 daltons.

4. Cloning of BpmI restriction endonuclease gene (BpmIRM) by inverse PCR.

In accordance with the present invention, it was determined that there was one partial open reading frame upstream of BpmIM1 gene that has 31% amino acid sequence identity to another restriction enzyme Eco57I with similar recognition sequence (Eco57I recognition sequence: 5'CTGAAG N16/N14; A. Janulaitis et al. *Nucl. Acids Res.* 20:6051–6056 (1992); BpmI recognition sequence: 5'CTGGAG N16/N14). Genomic DNA is digested with restriction enzymes. The digested DNA is ligated at a low DNA concentration and then used for inverse PCR amplification of BpmIR gene. Inverse PCR products are derived, gel-purified from low-melting agarose and sequenced. After four rounds of inverse PCR reactions, an open reading frame of 3,030 bp was found upstream of BpmI M1 methylase gene, which encoded a 1,009-amino acid protein with predicted molecular mass of 116,891 daltons. This is one of the largest restriction enzyme discovered so far. By amino acid sequence comparison of BpmI endonuclease with all known proteins in GenBank protein database, it is discovered that BpmI endonuclease is a fusion of two distinct elements with a possible structural domains of restriction-methylation-specificity (R-M-S). This domain organization is analogous to the type I restriction-modification system with three distinct subunits, restriction, methylation, and specificity (R, M, and S). Because BpmI is quite distinct to other type IIs restriction enzymes, it is suggested that BpmI belongs to a subgroup of type II restriction enzymes called type IIf (f stands for fusion of restriction-modification-specificity domains).

5. Expression of BpmIM1 gene in E. coli.

Two primers are synthesized to amplify BpmIM1 gene in PCR. Following digestion with BamHI and SphI, the PCR product is ligated into pACYC184 with the compatible ends. The ligated DNA is transformed into ER2566 competent cells. Plasmids with BpmIM1 gene inserts are tested for resistance to BpmI digestion. Two out of 18 clones were found to be resistant to BpmI digestion, indicating efficient BpmI M1 expression in E. coli cells and BpmI site modification on the expression plasmid. The host cell ER2566 [pACYC-BpmIM1] is used for expression of BpmIRM gene.

BpmI M1 methylase also modifies XhoI site. XhoI recognition sequence 5'CTCGAG3' is similar to BpmI recognition sequence 5'CTGGAG3' with only one base difference. It is concluded that BpmI M1 methylase may recognize the sequence 5'CTNNAG3' and modify the adenine base to generate N6-adenine in the symmetric sequence.

6. Expression of BpmIRM gene in E. coli using a T7 expression vector.

The 3,030-bp BpmIRM gene was amplified in PCR using Taq DNA polymerase, digested with BamHI and ligated into BamHI-digested T7 expression vectors pAII17 and pET21a. After transformation of the ligated DNA into ER2566 [pACYC-BpmIM1], transformants were screened for the endonuclease gene insert. Seven out of 72 clones contained the insert with correct orientation. However, no BpmI activity was detected in cell extracts of IPTG-induced cells. This is probably due to mutations introduced during the PCR process.

To reduce the mutation frequency, Deep Vent® DNA polymerase was used in PCR reactions to amplify the 3030-bp BpmIRM gene. The PCR product was digested with BamHI and XbaI and ligated to T7 expression vectors pAII17 and pET21at. Eighteen out of 36 clones contain the correct size insert. Ten ml cell culture for all 18 clones were induced with IPTG and cell extracts were prepared and assayed for BpmI activity. Clone #4 displayed partial BpmI activity.

7. Partial purification of recombinant BpmI activity.

Figure 4:
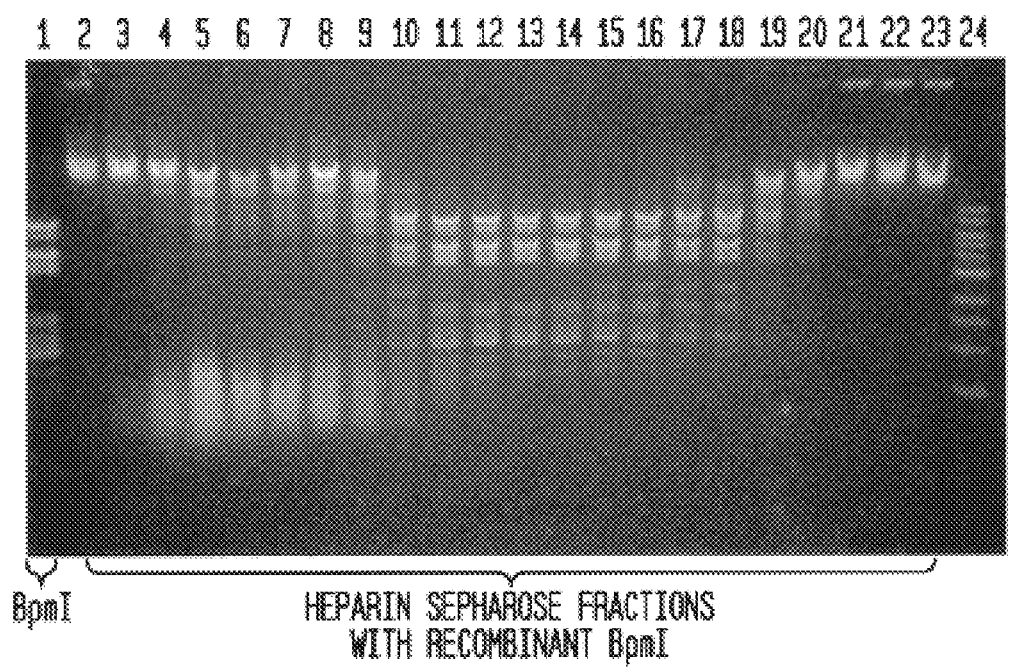
FIG. 4 Recombinant BpmI endonuclease activity in column fractions following heperin Sepharose chromatography. Lane 1: purified native BpmI endonuclease; lanes 2 to 23: heperin Sepharose column fractions. Fractions 11 to 14 gave rise to complete BpmI digestion of λ DNA. The remaining fractions contain no or partial BpmI activity. Lane 24: 1 kb DNA size marker.

Five hundred ml of cell culture was made for the expression clone #4 ER2566 [pACYC-BpmIM1, pET21at-BpmIRM]. Cell extract (40 ml) containing BpmI was purified through a heparin Sepharose column. Proteins were eluted with a NaCl gradient of 50 mM to 1 M. Fractions 6 to 27 are assayed for BpmI activity on λ DNA. It was found that fractions 15 to 18 contained the most active BpmI activity (FIG. 4). The yield was estimated at 1,800 units of BpmI per gram of wet E. coli cells. The specific activity was estimated at 24,000 units per mg of protein.

The present invention is further illustrated by the following Examples. These Examples are provided to aid in the understanding of the invention and are not construed as a limitation thereof.

The references cited above and below are hereby incorporated by reference herein.

EXAMPLE 1

Cloning of BpmI Restrection-modification System in E. coli

1. Preparation of genomic DNA and restriction digestion of genomic DNA.

Genomic DNA is prepared from Bacillus pumilus (New England Biolabs collection #711) by the standard procedure consisting of the following steps:

(a) cell lysis by addition of lysozyme (2 mg/ml final), sucrose (1% final), and 50 mM Tris-HCl, pH 8.0;

(b) cell lysis by addition of 10% SDS (final concentration 0.1%);

(c) cell lysis by addition of 1% Triton X-100 and 62 mM EDTA, 50 mM Tris-HCl, pH 8.0;

(d) phenol-CHCl$_3$ extraction of DNA 3 times (equal volume) and CHCl$_3$ extraction one time;

(e) DNA dialysis in 4 liters of TE buffer, change 3×; and (f) RNA was removed by RNAse A treatment and the genomic DNA was precipitated in ethanol and resupended in TE buffer;

Five μg genomic DNA was digested partially with 2, 1, 0.5, and 0.25 units of ApoI (recognition sequence R/AATTY) at 50° C. for 30 min. Genomic DNA fragments in the range of 2–10 kb were purified through a 1% low-melting agarose gel. Genomic and pBR322 DNA were also digested with AatII, BamHI, ClaI, EagI, EcoRI, HindIII, NdeI, NheI, SalI, and SphI, respectively. Genomic DNA fragments were ligated to pBR322 with compatible ends.

2. Construction of ApoI partial genomic DNA library and challenge of library with BpmI.

The ApoI partial DNA fragments were ligated to EcoRI digested and CIP treated pBR322 vector. The ligated DNA was dialyzed by drop dialysis on 4 L of distilled water and transferred into E. coli RR1 competent cells by electroporation. Ap$^R$ transformants were pooled and amplified. Plasmid DNA was prepared from the overnight cells and challenged with BpmI. Following BpmI digestion, the challenged DNA was transformed into RR1 cells. Ap$^R$ survivors were screened for resistance to BpmI digestion. A total of 36 plasmid mini-preparations were made. Two resistant clones, #18 and #26, were identified to be resistant to BpmI digestion. AatII, BamHI, ClaI, EagI, EcoRI, HindIII, NdeI, NheI, SalI, and SphI digested genomic DNA were also ligated to pBR322 with compatible ends and genomic DNA libraries were constructed. However, no apparent BpmI resistant clones were discovered from these libraries after screening more than 144 clones.

3. Subcloning and DNA sequencing of the resistant clone.

One resistant clone #26 contains an insert of about 3.1 kb. The forward and reverse primers of pUC19 were used to sequence the insert. Three ApoI and one HindIII fragments were gel-purified and subcloned in pUC19 and sequenced. The rest of the insert was sequenced by primer walking. A methylase gene with high homology to amino-methyltransferase (N6-adenine methylase) was found within the insert which was name BpmI M1 gene. The BpmIM1 gene is 1,650 bp, encoding a 549-amino acid protein with predicted molecular mass of 63,702 daltons.

4. Cloning of BpmI restriction endonuclease gene (BpmIRM) by inverse PCR.

There is one partial open reading frame upstream of BpmIM1 gene that has 31% amino acid sequence identity to another restriction enzyme Eco57I with similar recognition sequence (Eco57I recognition sequence: 5'CTGAAG N16/

N14; A. Janulaitis et al. *Nucl. Acids Res.* 20:6051–6056 (1992); BpmI recognition sequence: 5'CTGGAG N16/N14). Genomic DNA was digested with restriction enzymes AseI, BclI, HaeII, HpaII, MboI, MseI, NlaIII, PacI, and Tsp509I. The digested DNA was ligated at a low DNA concentration at 2 µg/ml and then used for inverse PCR amplification of BpmIR gene. The sequence of the inverse PCR primers was the following:

5' gtggaaacggaccgtattatggtt 3' (232-34) (SEQ ID NO:5)
5' caccagtaaataacaggttattcc 3' (232-35) (SEQ ID NO:6)

Inverse PCR conditions were 94° C. 1 min, 55° C. 1 min, 72° C. 2 min for 35 cycles. Inverse PCR products were derived from HaeIII and NlaIII templates, gel-purified from low-melting agarose and sequenced using primers 232-34 and 35.

The primers for second round of inverse PCR were the following:

5' ttcgtagcaagtacggtccatatcagt 3' (233-76) (SEQ ID NO:7)
5' ccgtatgtacttgataggaataacctg 3' (233-77) (SEQ ID NO:8)

Genomic DNA was digested with AseI, BclI, BsrFI, BstNI, EcoRI, HincII, HindIII, HpaII, NcoI, PacI, PvuI, TaqI, TfiI, and XbaI. The digested DNA was ligated at a low DNA concentration at 2 µg/ml and then used for inverse PCR amplification of BpmIR gene. Inverse PCR conditions were 94° C. 1 min, 55° C. 1 min, 72° C. 2 min for 35 cycles. Inverse PCR products were derived from AseI, HindIII, HpaII, and TaqI templates, gel-purified from low-melting agarose and sequenced using primers 233-76 and 77.

The primers for third round of inverse PCR were the following:

5' aggaactaagaaagttcatagctg 3' (234-61) (SEQ ID NO:9)
5' atgcggtattatataacccaacag 3' (234-62) (SEQ ID NO:10)

Genomic DNA was digested with AflIII, BspHI, BstNI, EcoRI, HaeII, HinP1I, HhaII, HindIII, StyI, and XmnI. The digested DNA was ligated at a low DNA concentration at 2 µg/ml and then used for inverse PCR amplification of BpmIR gene. Inverse PCR conditions were 94° C. 1 min, 55° C. 1 min, 72° C. 2 min for 35 cycles. Inverse PCR products were derived from HinP1I and XmnI templates, gel-purified from low-melting agarose and sequenced using primers 234-61 and 62.

The primers for the fourth round of inverse PCR were the following:

5' tgacgtcctcttcacctaattcgg 3' (235-50) (SEQ ID NO:11)
5' gagtttgtgaagatagaaccattg 3' (235-51) (SEQ ID NO:12)

Genomic DNA was digested with ApoI, BstBI, BstYI, ClaI, EcoRI, NdeI, RsaI, Sau3AI, SspI, TaqI, and XmnI. The digested DNA was ligated at a low DNA concentration at 2 µg/ml and then used for inverse PCR amplification of BpmIR gene. Inverse PCR conditions were 94° C. 1 min, 55° C. 1 min, 72° C. 2 min for 35 cycles. Inverse PCR products were derived from ApoI, ClaI, NdeI, RsaI, SspI, and TaqI templates, gel-purified from low-melting agarose and sequenced using primers 235-50 and 51. The ClaI fragment (2.4 kb) further extends upstream of BpmIRM gene. The rest of the ClaI fragment was sequenced using primer walking.

After four rounds of inverse PCR reactions, an open reading frame of 3,030 bp was found upstream of BpmI M1 methylase gene, which encodes a 1,009-amino acid protein with predicted molecular mass of 116,891 daltons. This is one of the largest restriction enzyme discovered so far. By amino acid sequence comparison of BpmI endonuclease with all known proteins in GenBank protein database, it was discovered that BpmI endonuclease is a fusion of two distinct elements with a possible structural domains of restriction-methylation-specificity (R-M-S). This domain organization is analogous to the type I restriction-modification system with three distinct subunits, restriction, methylation, and specificity (R, M, and S). Because BpmI is quite distinct to other type IIs restriction enzymes, it is proposed that BpmI belongs to a subgroup of type II restriction enzymes called type IIf (f stands for fusion of restriction-modification-specificity domains)

5. Expression of BpmIM1 gene in *E. coli.*

Two primers are synthesized to amplify BpmIM1 gene in PCR. The primer sequences are:

forward:
5' agccggatccggaggtaaataaatgaatcaattaattgaaaatgttaat 3' (238-177) (SEQ ID NO:13)

reverse:
5' aaggggggcatgcttatacttatttcttcgttctattgtttct 3' (238-178) (SEQ ID NO:14)

Following digestion with BamHI and SphI, the PCR product was ligated into pACYC184 with the compatible ends. The ligated DNA was transformed into ER2566 competent cells. $Cm^R$ transformants were plated at 37° C. overnight. Plasmids with BpmIM1 gene inserts were tested for resistance to BpmI digestion. Two out of 18 clones showed full resistance to BpmI digestion, indicating efficient BpmI M1 expression in *E. coli* cells and BpmI site modification on the expression plasmid. The host cell ER2566 [pACYC-BpmIM1] was used for expression of BpmIRM gene.

BpmI M1 methylase also modifies XhoI site. XhoI recognition sequence 5'CTCGAG3' is similar to BpmI recognition sequence 5'CTGGAG3' with only one base difference. It is concluded that BpmI M1 methylase may recognize the sequence 5'CTNNAG3' and modify the adenine base to generate N6-adenine in the symmetric recognition sequence.

6. Expression of BpmIRM gene in *E. coli* using a T7 expression vector.

Two primers were synthesized to amplify the BpmIRM gene. The primer sequences were:

5' caaggatccggaggtaaataaatgcatataagtgagttagtagataaatac 3' (247-217) (SEQ ID NO:15)
5' ttaggatcctcatttttcttctcctaacgccgctgt 3' (238-182) (SEQ ID NO:16)

The 3,030-bp BpmIRM gene was amplified in PCR using Taq DNA polymerase, digested with BamHI and ligated into BamHI-digested T7 expression vectors pAII17 and pET21a. After transformation of the ligated DNA into ER2566 [pACYC-BpmIM1], $Ap^R$ $Cm^R$ transformants were screened for the endonuclease gene insert. Seven out of 72 clones contained the insert with correct orientation. However, no BpmI activity was detected in cell extracts of IPTG-induced cells. This was probably due to mutations introduced during the PCR process.

To reduce the mutation frequency, Deep Vent® DNA polymerase was used in PCR reactions to amplify the 3,030-bp BpmIRM gene. The forward primer incorporated an XbaI site and its sequence is the following:

5' caccaatctagaggaggtaaataaatgcatataagtgagttagtagataaatac 3' (238-181) (SEQ ID NO:17)

PCR was performed using primers 238-181, 238-182, and Deep Vent® DNA polymerase. The PCR conditions were 94° C. 5 min for one cycle; 94° C. 1 min, 55° C. 1.5 min, 72° C. 8 min for 20 cycles. The PCR product was purified through a Qiagen spin column and digested with BamHI and XbaI and ligated to T7 expression vectors pAII17 and pET21 at with compatible ends. Eighteen out of 36 clones contain the correct size insert. Ten ml cell culture for all 18 clones containing inserts were induced with IPTG for 3 h and cell extracts were prepared by sonication and assayed for BpmI activity. Clone #4 displayed partial BpmI activity. Because this gene was derived by PCR cloning, the entire BpmIRM fusion gene was sequenced on both strands and it was confirmed to be wild type sequence.

7. Partial purification of recombinant BpmI activity.

Five hundred ml of cell culture was made for the expression clone #4 ER2566 [pACYC-BpmIM1, pET21at-BpmIRM]. The late log cells were induced with IPTG and Cell extract (40 ml) containing BpmI was purified through a heparin Sepharose column. Proteins were eluted with a NaCl gradient of 50 mM to 1 M. Fractions 6 to 27 contained the most protein concentration and were assayed for BpmI activity on λ DNA. It was found that fractions 15 to 18 contained the most active BpmI activity (FIG. 4). The yield was estimated at 1,800 units of BpmI per gram of wet E. coli cells. The specific activity was estimated at 24,000 units per mg of protein. Proteins from fractions 15 to 18 were analyzed on a SDS-PAGE gel and protein bands were stained with Gelcode blue stain. A protein band corresponding to ~115 kDa was detected on the protein gel, in close agreement with the predicted size of 117 kDa.

The E. coli strain ER2566 [pACYC-BpmIM1, pET21at-BpmIRM] has been deposited under the terms and conditions of the Budapest Treaty with the American Type Culture Collection on Oct. 12, 2000 and received Accession No. PTA-2598.

EXAMPLE 2

Deletion of the Methylase Portion of BpmI RM Fusion Protein

Two primers were synthesized to amplify the putative endonuclease domain with deletion of the methylase and specificity domains. The deletion clone thus contains only the R portion and the M and S portions were removed. The forward primer was 238-181 as described above. The reverse primer had the following sequence with a XhoI site at the 5' end:

5' tgaaatctcgagttatcctgatccacaacatatatctgctat 3' (244-95) (SEQ ID NO:18)

The deletion junction was in motif I of γ type N6 adenine methylase. The γ type N6 adenine methylases contain conserved motifs of X, I, II, III, IV, V, VI, VII, VIII. The specificity domain (TRD) is located after motif VIII. The BpmI deletion clone (BpmI-Δ#1) still carried motifs X and part of motif I. The specificity domain after motif VIII was also deleted (the remaining portion is shown in FIG. 1).

PCR was performed using primers 238-181 and 244-95 and Taq plus Vent® DNA polymerase (94° C. 1 min, 60° C. 1 min, and 72° C. 1 min for 25 cycles). The PCR product was digested with XbaI and XhoI and cloned into a T7 expression vector pET21b. Sixteen clones out of 36 screened contained the correct size insert and the cells were induced with IPTG for 3 h. Cell extract was prepared by sonication and assayed for BpmI activity on λ DNA. However, no apparent BpmI digestion pattern was detected. Only non-specific nuclease was detected in cell extract, resulting in a smearing of DNA substrate. It was concluded that deletion of the methylase and specificity portion of the BpmIRM fusion protein abolished BpmI restriction activity.

To further confirm the above result, another deletion clone was constructed that deleted methylase motifs IV, V, VI, VII, VIII, and the specificity domain. This EcoRI fragment deletion mutant contains 1,521 bp (507 amino acid) deletion at the C-terminus half of the fusion protein (BpmI-Δ#2). IPTG-induced cell extract of this mutant also did not display BpmI endonuclease activity.

To delete the specificity domain (target-recognizing domain, TRD), a HindIII fragment of 579 bp (193 amino acid) was deleted from the C-terminus of BpmI RM fusion endonuclease (BpmI-Δ#3). IPTG-induced cell extract of the TRD deletion mutant did not show any BpmI endonuclease activity. However, the mutant protein displayed non-specific nuclease activity. It was concluded that the specificity (TRD) domain is also required for BpmI endonuclease activity. Deletion of the specificity (TRD) domain may abolish or reduce its DNA binding affinity and specificity. By swapping in of other N6 methylase and specificity domains, one may be able to create new enzyme specificity.

EXAMPLE 3

Generation of New Enzyme Specificity Using BpmI RM Fusion Protein

Since BpmI endonuclease consists of three domains (R-M-S), it is possible to plug in other methylation-specificity domains to create a new enzyme specificity. The BpmIRM fusion gene is cloned in a T7 expression vector as described in Example 1. Plasmid DNA is prepared. The γ type N6 adenine methylases contain conserved motifs of X, I, II, III, IV, V, VI, VII, VIII (Malone T. et al. J. Mol.Biol 253:618–632 (1995)). Motifs X through VIII and TRD are deleted and a DNA linker coding for one or more bridging amino acids is inserted with a restriction site, preferably blunt (for example SmaI site). The number of amino acids will differ from one system to the next and can be determined by routine experimentation. The goal is to provide sufficient steric space for the introduction of the new M-S domains. DNA coding for other γ type N6 adenine methylases containing motifs of X, I, II, III, IV, V, VI, VII, VIII and TRD are ligated to the digested blunt site (in frame) of the BpmI deletion clone. The ligated DNA is transformed into a non-T7 expression vector. After the insert is verified, the plasmid containing new methylation-specificity domains is transformed into a T7 expression host and induced with IPTG. Cell extract is assayed on plasmid and phage DNA and analyzed for new restriction activity.

What is claimed is:

1. Isolated DNA coding for the BpmI restriction endonuclease, wherein the isolated DNA is obtainable from *Bacillus pumilus* (New England Biolabs collection #711).

2. A recombinant DNA vector comprising a vector into which a DNA segment encoding the BpmIRM restriction endonuclease has been inserted.

3. Isolated DNA encoding the BpmI restriction endonuclease and BpmI methylase M1, wherein the isolated DNA is obtainable from ATCC No. PTA-2598.

4. A cloning vector which comprises the isolated DNA of claim 3.

5. A host cell transformed by the vector of claims 2 or 4.

6. A method of producing recombinant BpmI restriction endonuclease comprising culturing a host cell transformed with the vector of claims 2 or 4 under conditions suitable for expression of said endonuclease.

* * * * *

UNITED STATES PATENT AND TRADEMARK OFFICE
CERTIFICATE OF CORRECTION

PATENT NO.     : 6,413,758 B1
DATED          : July 2, 2002
INVENTOR(S)    : Xu et al.

It is certified that error appears in the above-identified patent and that said Letters Patent is hereby corrected as shown below:

<u>Drawings,</u>
Figure 1, replace with new Figure 1.

<u>Column 3,</u>
Line 40, replace "porduct" with -- product --
Line 44, replace "Vent" with -- Vent® --

<u>Column 4,</u>
Line 45, replace "name" with -- named --

<u>Column 6,</u>
Line 59, replace "name" with -- named --

Signed and Sealed this

Second Day of March, 2004

JON W. DUDAS
*Acting Director of the United States Patent and Trademark Office*

SEQUENCE LISTING

<160> NUMBER OF SEQ ID NOS: 18

<210> SEQ ID NO 1
<211> LENGTH: 1650
<212> TYPE: DNA
<213> ORGANISM: Bacillus pumilus
<220> FEATURE:

-continued

```
<221> NAME/KEY: CDS
<222> LOCATION: (1)..(1650)

<400> SEQUENCE: 1 atg aat caa tta att gaa aat gtt aat cta caa aaa tta agg ggt ggg        48
Met Asn Gln Leu Ile Glu Asn Val Asn Leu Gln Lys Leu Arg Gly Gly
  1               5                  10                  15 tat tac acc cct aaa gtt att gct gac ttt tta tgt caa tgg agt att        96
Tyr Tyr Thr Pro Lys Val Ile Ala Asp Phe Leu Cys Gln Trp Ser Ile
             20                  25                  30 caa gat gac aca aag agt gta ctt gaa ccc agt tgt gga gat ggt aat       144
Gln Asp Asp Thr Lys Ser Val Leu Glu Pro Ser Cys Gly Asp Gly Asn
         35                  40                  45 ttt att gaa tcg gca ata ctt agg ttc aaa gaa ctt agt ata gat aat       192
Phe Ile Glu Ser Ala Ile Leu Arg Phe Lys Glu Leu Ser Ile Asp Asn
     50                  55                  60 gaa caa ctt aaa gga aga att aca gga gta gag cta att gaa gaa gaa       240
Glu Gln Leu Lys Gly Arg Ile Thr Gly Val Glu Leu Ile Glu Glu Glu
 65                  70                  75                  80 gct ttg aaa gtt caa aat cga gca aat gag ttg ggg gtt gat aaa aac       288
Ala Leu Lys Val Gln Asn Arg Ala Asn Glu Leu Gly Val Asp Lys Asn
                 85                  90                  95 tca ata gta aat agt gac ttc ttt caa ttt gta aaa gat aat aag aat       336
Ser Ile Val Asn Ser Asp Phe Phe Gln Phe Val Lys Asp Asn Lys Asn
            100                 105                 110 aaa aaa ttt gat act att att ggt aat cca cca ttc ata aga tac caa       384
Lys Lys Phe Asp Thr Ile Ile Gly Asn Pro Pro Phe Ile Arg Tyr Gln
        115                 120                 125 aac ttt cct gaa gag cat cgt agt ata gcc atg gaa atg atg gag gaa       432
Asn Phe Pro Glu Glu His Arg Ser Ile Ala Met Glu Met Met Glu Glu
    130                 135                 140 cta ggt tta aaa cct aat aaa ctt aca aat atc tgg gtt cca ttt cta       480
Leu Gly Leu Lys Pro Asn Lys Leu Thr Asn Ile Trp Val Pro Phe Leu
145                 150                 155                 160 gtg gta tct gct aca tta ctt aat gaa caa gga aag atg gct atg gtt       528
Val Val Ser Ala Thr Leu Leu Asn Glu Gln Gly Lys Met Ala Met Val
                165                 170                 175 ata ccg gct gaa tta ttt cag gta aag tat gca gca gaa aca aga att       576
Ile Pro Ala Glu Leu Phe Gln Val Lys Tyr Ala Ala Glu Thr Arg Ile
            180                 185                 190 ttt tta tca aag ttt ttc gat cgt atc act ata att aca ttt gaa aaa       624
Phe Leu Ser Lys Phe Phe Asp Arg Ile Thr Ile Ile Thr Phe Glu Lys
        195                 200                 205 ctt gtt ttt gaa aat atc caa cag gaa gtt ata cta ctt ctt tgt gaa       672
Leu Val Phe Glu Asn Ile Gln Gln Glu Val Ile Leu Leu Leu Cys Glu
    210                 215                 220 aag aaa gtt aat aaa ggt aaa gga att cgg gtt att gaa tgc gag aac       720
Lys Lys Val Asn Lys Gly Lys Gly Ile Arg Val Ile Glu Cys Glu Asn
225                 230                 235                 240 tta gat gga tta aat tcc att gat ttt gta gct ata aat ggt tca aat       768
Leu Asp Gly Leu Asn Ser Ile Asp Phe Val Ala Ile Asn Gly Ser Asn
                245                 250                 255 gtt aaa cct att gaa cac cgt act gaa aag tgg aca aag tat ttc tta       816
Val Lys Pro Ile Glu His Arg Thr Glu Lys Trp Thr Lys Tyr Phe Leu
            260                 265                 270 aac gaa gat gaa ata ctt ctt tta cag agt tta aag gaa gac aaa cgc       864
Asn Glu Asp Glu Ile Leu Leu Leu Gln Ser Leu Lys Glu Asp Lys Arg
        275                 280                 285
```

-continued

```
gtt aaa aat tgt aat gac tat ttt aag aca gaa gtt ggc tta gtt act        912
Val Lys Asn Cys Asn Asp Tyr Phe Lys Thr Glu Val Gly Leu Val Thr
    290                 295                 300 gga cga aac gaa ttc ttt atg atg aaa gaa aac caa gta aaa gaa tgg        960
Gly Arg Asn Glu Phe Phe Met Met Lys Glu Asn Gln Val Lys Glu Trp
305                 310                 315                 320 aat cta gaa gaa tat aca ata cct gtt aca ggt agg tcc aat cag tta      1008
Asn Leu Glu Glu Tyr Thr Ile Pro Val Thr Gly Arg Ser Asn Gln Leu
                325                 330                 335 aaa ggt ata aca ttt aca gaa aat gat ttt cat gaa aat tca atg gaa      1056
Lys Gly Ile Thr Phe Thr Glu Asn Asp Phe His Glu Asn Ser Met Glu
340                 345                 350 caa aag gca att cac cta ttt ttg cca cca gat gaa gat ttt gaa aag      1104
Gln Lys Ala Ile His Leu Phe Leu Pro Pro Asp Glu Asp Phe Glu Lys
            355                 360                 365 tta ccg att gag tgt caa aat tat atc aag tat ggg gaa gaa aaa ggc      1152
Leu Pro Ile Glu Cys Gln Asn Tyr Ile Lys Tyr Gly Glu Glu Lys Gly
    370                 375                 380 ttc cat caa ggc tat aaa acc aga att aga aaa cgt tgg tat ata act      1200
Phe His Gln Gly Tyr Lys Thr Arg Ile Arg Lys Arg Trp Tyr Ile Thr
385                 390                 395                 400 cca tct aga tgg gtt cca gat gct ttt gct tta aga cag gtt gat ggc      1248
Pro Ser Arg Trp Val Pro Asp Ala Phe Ala Leu Arg Gln Val Asp Gly
                405                 410                 415 tat cca aaa cta att tta aat gaa acc gac gct tct tct act gat aca      1296
Tyr Pro Lys Leu Ile Leu Asn Glu Thr Asp Ala Ser Ser Thr Asp Thr
                420                 425                 430 att cat agg gtt aga ttt aaa gaa ggt ata aat gaa aag tta gcc gta      1344
Ile His Arg Val Arg Phe Lys Glu Gly Ile Asn Glu Lys Leu Ala Val
            435                 440                 445 gtt tca ttt ttg aac tca ctc act ttt gca tct tca gaa ata acg ggg      1392
Val Ser Phe Leu Asn Ser Leu Thr Phe Ala Ser Ser Glu Ile Thr Gly
    450                 455                 460 aga agt tat ggt ggt ggt gtt atg aca ttc gaa cca act gaa att gga      1440
Arg Ser Tyr Gly Gly Gly Val Met Thr Phe Glu Pro Thr Glu Ile Gly
465                 470                 475                 480 gaa atc cta ata cct tcc ttt gat aac tta tcc att gat ttt gat aaa      1488
Glu Ile Leu Ile Pro Ser Phe Asp Asn Leu Ser Ile Asp Phe Asp Lys
                485                 490                 495 att gat gcc tta att cga gaa aag gag att gaa aaa gtc ctt gat att      1536
Ile Asp Ala Leu Ile Arg Glu Lys Glu Ile Glu Lys Val Leu Asp Ile
            500                 505                 510 gtt gat gaa gct tta ctt ata aaa tat cat ggg ttt agt gag aaa gaa      1584
Val Asp Glu Ala Leu Leu Ile Lys Tyr His Gly Phe Ser Glu Lys Glu
    515                 520                 525 gta aaa cag ctt cga ggg ata tgg aag aaa ctt tct cag aga aga aac      1632
Val Lys Gln Leu Arg Gly Ile Trp Lys Lys Leu Ser Gln Arg Arg Asn
530                 535                 540 aat aga acg aag aaa taa                                              1650
Asn Arg Thr Lys Lys
545                 550
```

<210> SEQ ID NO 2
<211> LENGTH: 549
<212> TYPE: PRT
<213> ORGANISM: Bacillus pumilus

<400> SEQUENCE: 2

```
Met Asn Gln Leu Ile Glu Asn Val Asn Leu Gln Lys Leu Arg Gly Gly
1               5                   10                  15
```

-continued

Tyr Tyr Thr Pro Lys Val Ile Ala Asp Phe Leu Cys Gln Trp Ser Ile
            20                  25                  30

Gln Asp Asp Thr Lys Ser Val Leu Glu Pro Ser Cys Gly Asp Gly Asn
        35                  40                  45

Phe Ile Glu Ser Ala Ile Leu Arg Phe Lys Glu Leu Ser Ile Asp Asn
    50                  55                  60

Glu Gln Leu Lys Gly Arg Ile Thr Gly Val Glu Leu Ile Glu Glu Glu
65                  70                  75                  80

Ala Leu Lys Val Gln Asn Arg Ala Asn Glu Leu Gly Val Asp Lys Asn
                85                  90                  95

Ser Ile Val Asn Ser Asp Phe Phe Gln Phe Val Lys Asp Asn Lys Asn
            100                 105                 110

Lys Lys Phe Asp Thr Ile Ile Gly Asn Pro Pro Phe Ile Arg Tyr Gln
        115                 120                 125

Asn Phe Pro Glu Glu His Arg Ser Ile Ala Met Glu Met Met Glu Glu
    130                 135                 140

Leu Gly Leu Lys Pro Asn Lys Leu Thr Asn Ile Trp Val Pro Phe Leu
145                 150                 155                 160

Val Val Ser Ala Thr Leu Leu Asn Glu Gln Gly Lys Met Ala Met Val
                165                 170                 175

Ile Pro Ala Glu Leu Phe Gln Val Lys Tyr Ala Ala Glu Thr Arg Ile
            180                 185                 190

Phe Leu Ser Lys Phe Phe Asp Arg Ile Thr Ile Thr Phe Glu Lys
        195                 200                 205

Leu Val Phe Glu Asn Ile Gln Gln Glu Val Ile Leu Leu Leu Cys Glu
    210                 215                 220

Lys Lys Val Asn Lys Gly Lys Gly Ile Arg Val Ile Glu Cys Glu Asn
225                 230                 235                 240

Leu Asp Gly Leu Asn Ser Ile Asp Phe Val Ala Ile Asn Gly Ser Asn
                245                 250                 255

Val Lys Pro Ile Glu His Arg Thr Glu Lys Trp Thr Lys Tyr Phe Leu
            260                 265                 270

Asn Glu Asp Glu Ile Leu Leu Leu Gln Ser Leu Lys Glu Asp Lys Arg
        275                 280                 285

Val Lys Asn Cys Asn Asp Tyr Phe Lys Thr Glu Val Gly Leu Val Thr
    290                 295                 300

Gly Arg Asn Glu Phe Phe Met Met Lys Glu Asn Gln Val Lys Glu Trp
305                 310                 315                 320

Asn Leu Glu Glu Tyr Thr Ile Pro Val Thr Gly Arg Ser Asn Gln Leu
                325                 330                 335

Lys Gly Ile Thr Phe Thr Glu Asn Asp Phe His Glu Asn Ser Met Glu
            340                 345                 350

Gln Lys Ala Ile His Leu Phe Leu Pro Pro Asp Glu Asp Phe Glu Lys
        355                 360                 365

Leu Pro Ile Glu Cys Gln Asn Tyr Ile Lys Tyr Gly Glu Glu Lys Gly
    370                 375                 380

Phe His Gln Gly Tyr Lys Thr Arg Ile Arg Lys Arg Trp Tyr Ile Thr
385                 390                 395                 400

Pro Ser Arg Trp Val Pro Asp Ala Phe Ala Leu Arg Gln Val Asp Gly
                405                 410                 415

Tyr Pro Lys Leu Ile Leu Asn Glu Thr Asp Ala Ser Ser Thr Asp Thr
            420                 425                 430

-continued

```
Ile His Arg Val Arg Phe Lys Glu Gly Ile Asn Glu Lys Leu Ala Val
        435                 440                 445

Val Ser Phe Leu Asn Ser Leu Thr Phe Ala Ser Ser Glu Ile Thr Gly
    450                 455                 460

Arg Ser Tyr Gly Gly Gly Val Met Thr Phe Glu Pro Thr Glu Ile Gly
465                 470                 475                 480

Glu Ile Leu Ile Pro Ser Phe Asp Asn Leu Ser Ile Asp Phe Asp Lys
                485                 490                 495

Ile Asp Ala Leu Ile Arg Glu Lys Glu Ile Glu Lys Val Leu Asp Ile
                500                 505                 510

Val Asp Glu Ala Leu Leu Ile Lys Tyr His Gly Phe Ser Glu Lys Glu
            515                 520                 525

Val Lys Gln Leu Arg Gly Ile Trp Lys Lys Leu Ser Gln Arg Arg Asn
        530                 535                 540

Asn Arg Thr Lys Lys
545
```

<210> SEQ ID NO 3
<211> LENGTH: 3030
<212> TYPE: DNA
<213> ORGANISM: Bacillus pumilus
<220> FEATURE:
<221> NAME/KEY: CDS
<222> LOCATION: (1)..(3030)

<400> SEQUENCE: 3

```
atg cat ata agt gag tta gta gat aaa tac aaa gcg cat aga agt act      48
Met His Ile Ser Glu Leu Val Asp Lys Tyr Lys Ala His Arg Ser Thr
  1               5                  10                  15 ttt tta aaa cca act tat aat gaa act caa cta agg aat gat ttt ata      96
Phe Leu Lys Pro Thr Tyr Asn Glu Thr Gln Leu Arg Asn Asp Phe Ile
             20                  25                  30 gac cca ctt cta aaa tct tta gga tgg gat gtt gat aat acc aaa gga     144
Asp Pro Leu Leu Lys Ser Leu Gly Trp Asp Val Asp Asn Thr Lys Gly
         35                  40                  45 aaa aca cat att cta aga gat gtc att caa gaa gaa tac ata gaa ata     192
Lys Thr His Ile Leu Arg Asp Val Ile Gln Glu Glu Tyr Ile Glu Ile
     50                  55                  60 aaa gat gag gag aca aag aaa aat cca gat tat aca ctt cgt ata aac     240
Lys Asp Glu Glu Thr Lys Lys Asn Pro Asp Tyr Thr Leu Arg Ile Asn
 65                  70                  75                  80 ggt acg aga aag ctg ttt gta gag gtt aag aaa ccg tct ttt aat att     288
Gly Thr Arg Lys Leu Phe Val Glu Val Lys Lys Pro Ser Phe Asn Ile
                 85                  90                  95 ttg aaa tca gct aaa gca gcc ttc caa aca aga aga tat ggt tgg agt     336
Leu Lys Ser Ala Lys Ala Ala Phe Gln Thr Arg Arg Tyr Gly Trp Ser
            100                 105                 110 gct aac ctt ggt att tca gta ctt aca aat ttc gag cat cta gtt att     384
Ala Asn Leu Gly Ile Ser Val Leu Thr Asn Phe Glu His Leu Val Ile
        115                 120                 125 tat gat tgt aga tat acg cct gac aaa tcc gac aat gaa cat att gct     432
Tyr Asp Cys Arg Tyr Thr Pro Asp Lys Ser Asp Asn Glu His Ile Ala
    130                 135                 140 aga tat aaa gtt ttc tct tac gag gaa tat gaa gaa gca ttt gat gaa     480
Arg Tyr Lys Val Phe Ser Tyr Glu Glu Tyr Glu Glu Ala Phe Asp Glu
145                 150                 155                 160 ata aag gat ata att tca tat gag tca gcc aac tca ggt gct ctg gac     528
Ile Lys Asp Ile Ile Ser Tyr Glu Ser Ala Asn Ser Gly Ala Leu Asp
                165                 170                 175
```

```
gaa atg ttt gat gta aat aca aga gtt ggt gaa acg ttt gac gag tat        576
Glu Met Phe Asp Val Asn Thr Arg Val Gly Glu Thr Phe Asp Glu Tyr
        180                 185                 190 ttt tta cag caa att gag aat tgg cgc gaa aag cta gct aaa act gca        624
Phe Leu Gln Gln Ile Glu Asn Trp Arg Glu Lys Leu Ala Lys Thr Ala
        195                 200                 205 att aaa aat aac acc gaa tta ggt gaa gag gac gtc aat ttt att gtc        672
Ile Lys Asn Asn Thr Glu Leu Gly Glu Glu Asp Val Asn Phe Ile Val
        210                 215                 220 caa aga cta tta aac aga att att ttt ctt aga gtt tgt gaa gat aga        720
Gln Arg Leu Leu Asn Arg Ile Ile Phe Leu Arg Val Cys Glu Asp Arg
225                 230                 235                 240 acc att gaa aaa tat gaa aca att aaa agt ata aaa aac tat gag gaa        768
Thr Ile Glu Lys Tyr Glu Thr Ile Lys Ser Ile Lys Asn Tyr Glu Glu
                245                 250                 255 tta aaa gat ctg ttt caa aag tct gat agg aaa ttt aat tca ggt ctc        816
Leu Lys Asp Leu Phe Gln Lys Ser Asp Arg Lys Phe Asn Ser Gly Leu
            260                 265                 270 ttt gac ttc ata gat gat acg ctc ttg ctt gag gtt gaa att gat tcg        864
Phe Asp Phe Ile Asp Asp Thr Leu Leu Leu Glu Val Glu Ile Asp Ser
            275                 280                 285 aat gta ttg ata gaa att ttt agt gat tta tat ttc cca caa agc cca        912
Asn Val Leu Ile Glu Ile Phe Ser Asp Leu Tyr Phe Pro Gln Ser Pro
        290                 295                 300 tat gat ttt tct gtt gtc gat cca aca ata tta agc cag ata tat gaa        960
Tyr Asp Phe Ser Val Val Asp Pro Thr Ile Leu Ser Gln Ile Tyr Glu
305                 310                 315                 320 cgt ttt cta ggt caa gaa ata att ata gag tca ggt ggt aca ttt cac       1008
Arg Phe Leu Gly Gln Glu Ile Ile Ile Glu Ser Gly Gly Thr Phe His
                325                 330                 335 att acg gag tca cca gaa gtt gcg gcg tcc aat ggt gtt gtt cca act       1056
Ile Thr Glu Ser Pro Glu Val Ala Ala Ser Asn Gly Val Val Pro Thr
            340                 345                 350 cca aaa att atc gtc gaa cag ata gtg aaa gac act tta acg ccc ctt       1104
Pro Lys Ile Ile Val Glu Gln Ile Val Lys Asp Thr Leu Thr Pro Leu
            355                 360                 365 acg gaa ggc aaa aaa ttt aat gag cta tgt aac tta aaa ata gca gat       1152
Thr Glu Gly Lys Lys Phe Asn Glu Leu Cys Asn Leu Lys Ile Ala Asp
        370                 375                 380 ata tgt tgt gga tca gga act ttc cta att tca agt tat gac ttt cta       1200
Ile Cys Cys Gly Ser Gly Thr Phe Leu Ile Ser Ser Tyr Asp Phe Leu
385                 390                 395                 400 gta gag aaa gta atg gaa aag ata ata gaa gag aac atc gat gat tca       1248
Val Glu Lys Val Met Glu Lys Ile Ile Glu Glu Asn Ile Asp Asp Ser
                405                 410                 415 gat tta gta tat gaa act gaa gaa ggg cta att ttg aca ctt aaa gca       1296
Asp Leu Val Tyr Glu Thr Glu Glu Gly Leu Ile Leu Thr Leu Lys Ala
            420                 425                 430 aaa aga aat atc ttg gag aat aat ttg ttt ggt gtt gat gtt aat cca       1344
Lys Arg Asn Ile Leu Glu Asn Asn Leu Phe Gly Val Asp Val Asn Pro
        435                 440                 445 tac gct gtt gaa gta gct gag ttc agt tta tta tta aag cta tta gaa       1392
Tyr Ala Val Glu Val Ala Glu Phe Ser Leu Leu Leu Lys Leu Leu Glu
    450                 455                 460 ggt gag aat gag gca tcg gtt aat aat ttc att cac gag cat gag gat       1440
Gly Glu Asn Glu Ala Ser Val Asn Asn Phe Ile His Glu His Glu Asp
465                 470                 475                 480 aaa ata tta ccg gat tta aca tct att att aaa tgt gga aac agc tta       1488
Lys Ile Leu Pro Asp Leu Thr Ser Ile Ile Lys Cys Gly Asn Ser Leu
                485                 490                 495
```

```
gta gat aat aag ttt ttt gaa ttc atg cca gaa tcg tta gag gac gat    1536
Val Asp Asn Lys Phe Phe Glu Phe Met Pro Glu Ser Leu Glu Asp Asp
            500                 505                 510 gaa atc tta ttt aag gct aat cca ttt gaa tgg gaa gag gag ttt cca    1584
Glu Ile Leu Phe Lys Ala Asn Pro Phe Glu Trp Glu Glu Glu Phe Pro
        515                 520                 525 gat att atg gca aat ggt ggc ttt gat gct att ata gga aat cca cct    1632
Asp Ile Met Ala Asn Gly Gly Phe Asp Ala Ile Ile Gly Asn Pro Pro
    530                 535                 540 tat gtt cga ata cag aac atg aaa aaa tat agt cct gag gaa att gaa    1680
Tyr Val Arg Ile Gln Asn Met Lys Lys Tyr Ser Pro Glu Glu Ile Glu
545                 550                 555                 560 tat tat caa tca aaa gac tct gaa tat act gtt gca aaa aaa gaa aca    1728
Tyr Tyr Gln Ser Lys Asp Ser Glu Tyr Thr Val Ala Lys Lys Glu Thr
                565                 570                 575 gtt gac aag tat ttt tta ttt att gag aga gca tta ata tta ctc aat    1776
Val Asp Lys Tyr Phe Leu Phe Ile Glu Arg Ala Leu Ile Leu Leu Asn
            580                 585                 590 cct act ggg ctg ttg ggt tat ata ata ccg cat aaa ttc ttt att aca    1824
Pro Thr Gly Leu Leu Gly Tyr Ile Ile Pro His Lys Phe Phe Ile Thr
        595                 600                 605 aaa ggt ggt aag gaa cta aga aag ttc ata gct gaa aaa cat caa ata    1872
Lys Gly Gly Lys Glu Leu Arg Lys Phe Ile Ala Glu Lys His Gln Ile
    610                 615                 620 tca aaa att ata aat ttt ggt gtt aca cag gtc ttt cca gga aga gcg    1920
Ser Lys Ile Ile Asn Phe Gly Val Thr Gln Val Phe Pro Gly Arg Ala
625                 630                 635                 640 aca tat acg gct att tta att atc caa gca aat aaa atg gca cag ttc    1968
Thr Tyr Thr Ala Ile Leu Ile Ile Gln Ala Asn Lys Met Ala Gln Phe
                645                 650                 655 aag tat aag aaa gta agt aat ata tca gca gaa acc cta gat tct gaa    2016
Lys Tyr Lys Lys Val Ser Asn Ile Ser Ala Glu Thr Leu Asp Ser Glu
            660                 665                 670 gaa aat acg tgt gtt tat agc tca gaa aag tat aat tct gac cct tgg    2064
Glu Asn Thr Cys Val Tyr Ser Ser Glu Lys Tyr Asn Ser Asp Pro Trp
        675                 680                 685 ata ttt tta tct cct gaa aca gaa gct gtt ttt act aaa ttt aca gaa    2112
Ile Phe Leu Ser Pro Glu Thr Glu Ala Val Phe Thr Lys Phe Thr Glu
    690                 695                 700 gct caa ttt gag aaa ctt gga gaa atc act gat ata agt gta gga cta    2160
Ala Gln Phe Glu Lys Leu Gly Glu Ile Thr Asp Ile Ser Val Gly Leu
705                 710                 715                 720 caa aca agc gct gat aaa ata tat att ttt att cct gaa aat gaa act    2208
Gln Thr Ser Ala Asp Lys Ile Tyr Ile Phe Ile Pro Glu Asn Glu Thr
                725                 730                 735 tca gat aca tat ata ttt aat tat aaa ggg aaa aga tat gaa ata gaa    2256
Ser Asp Thr Tyr Ile Phe Asn Tyr Lys Gly Lys Arg Tyr Glu Ile Glu
            740                 745                 750 aaa tct ata tgt tgc cca gct atc tat gac tta tct ttt ggt tct ttt    2304
Lys Ser Ile Cys Cys Pro Ala Ile Tyr Asp Leu Ser Phe Gly Ser Phe
        755                 760                 765 gaa agc att cag gga aat gca caa atg ata ttc cct tat gaa atc aga    2352
Glu Ser Ile Gln Gly Asn Ala Gln Met Ile Phe Pro Tyr Glu Ile Arg
    770                 775                 780 gat gaa gaa gca tat cta cta gag gaa gaa acg ctt gaa aat gat tat    2400
Asp Glu Glu Ala Tyr Leu Leu Glu Glu Glu Thr Leu Glu Asn Asp Tyr
785                 790                 795                 800 cct ctt gct tgg aat tat ttg aat gag ttt aaa gaa gct ctt gaa aaa    2448
Pro Leu Ala Trp Asn Tyr Leu Asn Glu Phe Lys Glu Ala Leu Glu Lys
```

|  |  |  |  |  |  |  |  |  |  |  |  |  |  |  |  |
|---|---|---|---|---|---|---|---|---|---|---|---|---|---|---|---|
|  |  |  | 805 |  |  |  | 810 |  |  |  | 815 |  |  |  |  |
| aga | agc | tta | caa | ggc | cgt | aat | ccg | aaa | tgg | tat | caa | tat | ggt | cgg | tcc | 2496 |
| Arg | Ser | Leu | Gln | Gly | Arg | Asn | Pro | Lys | Trp | Tyr | Gln | Tyr | Gly | Arg | Ser |  |
|  |  |  | 820 |  |  |  | 825 |  |  |  | 830 |  |  |  |  |
| caa | agt | tta | tca | aaa | ttt | cat | gat | aaa | gaa | aaa | ctg | ata | tgg | acc | gta | 2544 |
| Gln | Ser | Leu | Ser | Lys | Phe | His | Asp | Lys | Glu | Lys | Leu | Ile | Trp | Thr | Val |  |
|  |  |  | 835 |  |  |  | 840 |  |  |  | 845 |  |  |  |  |
| ctt | gct | acg | aaa | ccc | ccg | tat | gta | ctt | gat | agg | aat | aac | ctg | tta | ttt | 2592 |
| Leu | Ala | Thr | Lys | Pro | Pro | Tyr | Val | Leu | Asp | Arg | Asn | Asn | Leu | Leu | Phe |  |
|  | 850 |  |  |  |  | 855 |  |  |  |  | 860 |  |  |  |  |
| act | ggt | ggt | gga | aac | gga | ccg | tat | tat | ggt | tta | att | aac | caa | tct | att | 2640 |
| Thr | Gly | Gly | Gly | Asn | Gly | Pro | Tyr | Tyr | Gly | Leu | Ile | Asn | Gln | Ser | Ile |  |
| 865 |  |  |  |  | 870 |  |  |  |  | 875 |  |  |  |  | 880 |  |
| tac | tct | ttg | cat | tat | ttt | tta | ggt | att | ctt | tca | cat | cct | gta | ata | gaa | 2688 |
| Tyr | Ser | Leu | His | Tyr | Phe | Leu | Gly | Ile | Leu | Ser | His | Pro | Val | Ile | Glu |  |
|  |  |  |  | 885 |  |  |  |  | 890 |  |  |  |  | 895 |  |  |
| agt | atg | gta | aaa | gca | agg | gcc | agt | gaa | ttt | agg | gga | tca | tat | tat | tct | 2736 |
| Ser | Met | Val | Lys | Ala | Arg | Ala | Ser | Glu | Phe | Arg | Gly | Ser | Tyr | Tyr | Ser |  |
|  |  |  | 900 |  |  |  | 905 |  |  |  | 910 |  |  |  |  |
| cat | gga | aaa | caa | ttt | att | gag | aaa | atc | cca | att | aga | aag | att | gat | ttt | 2784 |
| His | Gly | Lys | Gln | Phe | Ile | Glu | Lys | Ile | Pro | Ile | Arg | Lys | Ile | Asp | Phe |  |
|  |  |  | 915 |  |  |  | 920 |  |  |  | 925 |  |  |  |  |
| gat | gat | caa | gat | gag | gta | gac | aaa | tat | aat | acg | gtg | gtc | aca | aca | gta | 2832 |
| Asp | Asp | Gln | Asp | Glu | Val | Asp | Lys | Tyr | Asn | Thr | Val | Thr | Thr | Val |  |  |
|  | 930 |  |  |  |  | 935 |  |  |  |  | 940 |  |  |  |  |
| gaa | aaa | tta | att | ata | act | acc | gat | aga | att | aaa | agt | gag | agc | aat | gga | 2880 |
| Glu | Lys | Leu | Ile | Ile | Thr | Thr | Asp | Arg | Ile | Lys | Ser | Glu | Ser | Asn | Gly |  |
| 945 |  |  |  |  | 950 |  |  |  |  | 955 |  |  |  |  | 960 |  |
| ccc | cgg | agg | aga | atg | tta | aga | aga | agg | tta | gat | gct | ttg | tct | aat | caa | 2928 |
| Pro | Arg | Arg | Arg | Met | Leu | Arg | Arg | Arg | Leu | Asp | Ala | Leu | Ser | Asn | Gln |  |
|  |  |  |  | 965 |  |  |  |  | 970 |  |  |  |  | 975 |  |  |
| ctt | atc | cag | gtt | att | aat | gaa | ctt | tat | aat | atc | agt | gac | gaa | gaa | tat | 2976 |
| Leu | Ile | Gln | Val | Ile | Asn | Glu | Leu | Tyr | Asn | Ile | Ser | Asp | Glu | Glu | Tyr |  |
|  |  |  | 980 |  |  |  | 985 |  |  |  | 990 |  |  |  |  |
| acg | aca | gtt | ttg | aat | gat | gaa | atg | ttg | aca | gcg | gcg | tta | gga | gaa | gaa | 3024 |
| Thr | Thr | Val | Leu | Asn | Asp | Glu | Met | Leu | Thr | Ala | Ala | Leu | Gly | Glu | Glu |  |
|  |  |  | 995 |  |  |  | 1000 |  |  |  | 1005 |  |  |  |  |
| aaa | tga |  |  |  |  |  |  |  |  |  |  |  |  |  |  | 3030 |
| Lys |  |  |  |  |  |  |  |  |  |  |  |  |  |  |  |  |
| 1010 |  |  |  |  |  |  |  |  |  |  |  |  |  |  |  |  |

<210> SEQ ID NO 4
<211> LENGTH: 1009
<212> TYPE: PRT
<213> ORGANISM: Bacillus pumilus

<400> SEQUENCE: 4

Met His Ile Ser Glu Leu Val Asp Lys Tyr Lys Ala His Arg Ser Thr
1               5                   10                  15

Phe Leu Lys Pro Thr Tyr Asn Glu Thr Gln Leu Arg Asn Asp Phe Ile
                20                  25                  30

Asp Pro Leu Leu Lys Ser Leu Gly Trp Asp Val Asp Asn Thr Lys Gly
            35                  40                  45

Lys Thr His Ile Leu Arg Asp Val Ile Gln Glu Glu Tyr Ile Glu Ile
        50                  55                  60

Lys Asp Glu Glu Thr Lys Lys Asn Pro Asp Tyr Thr Leu Arg Ile Asn
65                  70                  75                  80

Gly Thr Arg Lys Leu Phe Val Glu Val Lys Lys Pro Ser Phe Asn Ile
                85                  90                  95

-continued

```
Leu Lys Ser Ala Lys Ala Ala Phe Gln Thr Arg Arg Tyr Gly Trp Ser
            100                 105                 110
Ala Asn Leu Gly Ile Ser Val Leu Thr Asn Phe Glu His Leu Val Ile
        115                 120                 125
Tyr Asp Cys Arg Tyr Thr Pro Asp Lys Ser Asp Asn Glu His Ile Ala
    130                 135                 140
Arg Tyr Lys Val Phe Ser Tyr Glu Glu Tyr Glu Ala Phe Asp Glu
145                 150                 155                 160
Ile Lys Asp Ile Ile Ser Tyr Glu Ser Ala Asn Ser Gly Ala Leu Asp
                165                 170                 175
Glu Met Phe Asp Val Asn Thr Arg Val Gly Glu Thr Phe Asp Glu Tyr
            180                 185                 190
Phe Leu Gln Gln Ile Glu Asn Trp Arg Glu Lys Leu Ala Lys Thr Ala
        195                 200                 205
Ile Lys Asn Asn Thr Glu Leu Gly Glu Glu Asp Val Asn Phe Ile Val
    210                 215                 220
Gln Arg Leu Leu Asn Arg Ile Ile Phe Leu Arg Val Cys Glu Asp Arg
225                 230                 235                 240
Thr Ile Glu Lys Tyr Glu Thr Ile Lys Ser Ile Lys Asn Tyr Glu Glu
                245                 250                 255
Leu Lys Asp Leu Phe Gln Lys Ser Asp Arg Lys Phe Asn Ser Gly Leu
            260                 265                 270
Phe Asp Phe Ile Asp Asp Thr Leu Leu Leu Glu Val Glu Ile Asp Ser
        275                 280                 285
Asn Val Leu Ile Glu Ile Phe Ser Asp Leu Tyr Phe Pro Gln Ser Pro
    290                 295                 300
Tyr Asp Phe Ser Val Val Asp Pro Thr Ile Leu Ser Gln Ile Tyr Glu
305                 310                 315                 320
Arg Phe Leu Gly Gln Glu Ile Ile Ile Glu Ser Gly Gly Thr Phe His
                325                 330                 335
Ile Thr Glu Ser Pro Glu Val Ala Ala Ser Asn Gly Val Val Pro Thr
            340                 345                 350
Pro Lys Ile Ile Val Glu Gln Ile Val Lys Asp Thr Leu Thr Pro Leu
        355                 360                 365
Thr Glu Gly Lys Lys Phe Asn Glu Leu Cys Asn Leu Lys Ile Ala Asp
    370                 375                 380
Ile Cys Cys Gly Ser Gly Thr Phe Leu Ile Ser Ser Tyr Asp Phe Leu
385                 390                 395                 400
Val Glu Lys Val Met Glu Lys Ile Ile Glu Glu Asn Ile Asp Asp Ser
                405                 410                 415
Asp Leu Val Tyr Glu Thr Glu Glu Gly Leu Ile Leu Thr Leu Lys Ala
            420                 425                 430
Lys Arg Asn Ile Leu Glu Asn Asn Leu Phe Gly Val Asp Val Asn Pro
        435                 440                 445
Tyr Ala Val Glu Val Ala Glu Phe Ser Leu Leu Leu Lys Leu Leu Glu
    450                 455                 460
Gly Glu Asn Glu Ala Ser Val Asn Asn Phe Ile His Glu His Glu Asp
465                 470                 475                 480
Lys Ile Leu Pro Asp Leu Thr Ser Ile Ile Lys Cys Gly Asn Ser Leu
                485                 490                 495
Val Asp Asn Lys Phe Phe Glu Phe Met Pro Glu Ser Leu Glu Asp Asp
            500                 505                 510
```

```
Glu Ile Leu Phe Lys Ala Asn Pro Phe Glu Trp Glu Glu Phe Pro
            515                 520                 525

Asp Ile Met Ala Asn Gly Gly Phe Asp Ala Ile Ile Gly Asn Pro Pro
        530                 535                 540

Tyr Val Arg Ile Gln Asn Met Lys Lys Tyr Ser Pro Glu Glu Ile Glu
545                 550                 555                 560

Tyr Tyr Gln Ser Lys Asp Ser Glu Tyr Thr Val Ala Lys Lys Glu Thr
                565                 570                 575

Val Asp Lys Tyr Phe Leu Phe Ile Glu Arg Ala Leu Ile Leu Leu Asn
            580                 585                 590

Pro Thr Gly Leu Leu Gly Tyr Ile Ile Pro His Lys Phe Phe Ile Thr
        595                 600                 605

Lys Gly Gly Lys Glu Leu Arg Lys Phe Ile Ala Glu Lys His Gln Ile
    610                 615                 620

Ser Lys Ile Ile Asn Phe Gly Val Thr Gln Val Phe Pro Gly Arg Ala
625                 630                 635                 640

Thr Tyr Thr Ala Ile Leu Ile Ile Gln Ala Asn Lys Met Ala Gln Phe
                645                 650                 655

Lys Tyr Lys Lys Val Ser Asn Ile Ser Ala Glu Thr Leu Asp Ser Glu
            660                 665                 670

Glu Asn Thr Cys Val Tyr Ser Ser Glu Lys Tyr Asn Ser Asp Pro Trp
        675                 680                 685

Ile Phe Leu Ser Pro Glu Thr Glu Ala Val Phe Thr Lys Phe Thr Glu
    690                 695                 700

Ala Gln Phe Glu Lys Leu Gly Glu Ile Thr Asp Ile Ser Val Gly Leu
705                 710                 715                 720

Gln Thr Ser Ala Asp Lys Ile Tyr Ile Phe Ile Pro Glu Asn Glu Thr
                725                 730                 735

Ser Asp Thr Tyr Ile Phe Asn Tyr Lys Gly Lys Arg Tyr Glu Ile Glu
            740                 745                 750

Lys Ser Ile Cys Cys Pro Ala Ile Tyr Asp Leu Ser Phe Gly Ser Phe
        755                 760                 765

Glu Ser Ile Gln Gly Asn Ala Gln Met Ile Phe Pro Tyr Glu Ile Arg
    770                 775                 780

Asp Glu Glu Ala Tyr Leu Leu Glu Glu Glu Thr Leu Glu Asn Asp Tyr
785                 790                 795                 800

Pro Leu Ala Trp Asn Tyr Leu Asn Glu Phe Lys Glu Ala Leu Glu Lys
                805                 810                 815

Arg Ser Leu Gln Gly Arg Asn Pro Lys Trp Tyr Gln Tyr Gly Arg Ser
            820                 825                 830

Gln Ser Leu Ser Lys Phe His Asp Lys Glu Lys Leu Ile Trp Thr Val
        835                 840                 845

Leu Ala Thr Lys Pro Pro Tyr Val Leu Asp Arg Asn Asn Leu Leu Phe
    850                 855                 860

Thr Gly Gly Asn Gly Pro Tyr Tyr Gly Leu Ile Asn Gln Ser Ile
865                 870                 875                 880

Tyr Ser Leu His Tyr Phe Leu Gly Ile Leu Ser His Pro Val Ile Glu
                885                 890                 895

Ser Met Val Lys Ala Arg Ala Ser Glu Phe Arg Gly Ser Tyr Tyr Ser
            900                 905                 910

His Gly Lys Gln Phe Ile Glu Lys Ile Pro Ile Arg Lys Ile Asp Phe
        915                 920                 925
```

```
Asp Asp Gln Asp Glu Val Asp Lys Tyr Asn Thr Val Val Thr Thr Val
        930                 935                 940

Glu Lys Leu Ile Ile Thr Thr Asp Arg Ile Lys Ser Glu Ser Asn Gly
945                 950                 955                 960

Pro Arg Arg Arg Met Leu Arg Arg Leu Asp Ala Leu Ser Asn Gln
                965                 970                 975

Leu Ile Gln Val Ile Asn Glu Leu Tyr Asn Ile Ser Asp Glu Glu Tyr
            980                 985                 990

Thr Thr Val Leu Asn Asp Glu Met Leu Thr Ala Ala Leu Gly Glu Glu
        995                 1000                1005

Lys

<210> SEQ ID NO 5
<211> LENGTH: 24
<212> TYPE: DNA
<213> ORGANISM: Bacillus pumilus

<400> SEQUENCE: 5
gtggaaacgg accgtattat ggtt                                          24

<210> SEQ ID NO 6
<211> LENGTH: 24
<212> TYPE: DNA
<213> ORGANISM: Bacillus pumilus

<400> SEQUENCE: 6
caccagtaaa taacaggtta ttcc                                          24

<210> SEQ ID NO 7
<211> LENGTH: 27
<212> TYPE: DNA
<213> ORGANISM: Bacillus pumilus

<400> SEQUENCE: 7
ttcgtagcaa gtacggtcca tatcagt                                       27

<210> SEQ ID NO 8
<211> LENGTH: 27
<212> TYPE: DNA
<213> ORGANISM: Bacillus pumilus

<400> SEQUENCE: 8
ccgtatgtac ttgataggaa taacctg                                       27

<210> SEQ ID NO 9
<211> LENGTH: 24
<212> TYPE: DNA
<213> ORGANISM: Bacillus pumilus

<400> SEQUENCE: 9
aggaactaag aaagttcata gctg                                          24

<210> SEQ ID NO 10
<211> LENGTH: 24
<212> TYPE: DNA
<213> ORGANISM: Bacillus pumilus

<400> SEQUENCE: 10
atgcggtatt atataaccca acag                                          24
```

-continued

```
<210> SEQ ID NO 11
<211> LENGTH: 24
<212> TYPE: DNA
<213> ORGANISM: Bacillus pumilus

<400> SEQUENCE: 11
tgacgtcctc ttcacctaat tcgg                                              24

<210> SEQ ID NO 12
<211> LENGTH: 24
<212> TYPE: DNA
<213> ORGANISM: Bacillus pumilus

<400> SEQUENCE: 12
gagtttgtga agatagaacc attg                                              24

<210> SEQ ID NO 13
<211> LENGTH: 48
<212> TYPE: DNA
<213> ORGANISM: Bacillus pumilus

<400> SEQUENCE: 13
agcggatccg gaggtaaata aatgaatcaa ttaattgaaa atgttaat                    48

<210> SEQ ID NO 14
<211> LENGTH: 42
<212> TYPE: DNA
<213> ORGANISM: Bacillus pumilus

<400> SEQUENCE: 14 aaggggcat gcttatactt atttcttcgt tctattgttt ct                           42

<210> SEQ ID NO 15
<211> LENGTH: 51
<212> TYPE: DNA
<213> ORGANISM: Bacillus pumilus

<400> SEQUENCE: 15
caaggatccg gaggtaaata aatgcatata agtgagttag tagataaata c                51

<210> SEQ ID NO 16
<211> LENGTH: 36
<212> TYPE: DNA
<213> ORGANISM: Bacillus pumilus

<400> SEQUENCE: 16
ttaggatcct cattttctt ctcctaacgc cgctgt                                  36

<210> SEQ ID NO 17
<211> LENGTH: 54
<212> TYPE: DNA
<213> ORGANISM: Bacillus pumilus

<400> SEQUENCE: 17
caccaatcta gaggaggtaa ataaatgcat ataagtgagt tagtagataa atac             54

<210> SEQ ID NO 18
<211> LENGTH: 42
<212> TYPE: DNA
<213> ORGANISM: Bacillus pumilus

<400> SEQUENCE: 18
tgaaatctcg agttatcctg atccacaaca tatatctgct at                          42
```